US012318307B2

(12) United States Patent
Eisen et al.

(10) Patent No.: US 12,318,307 B2
(45) Date of Patent: Jun. 3, 2025

(54) ADJUSTABLE SPINAL IMPLANTS, ASSOCIATED INSTRUMENTS AND METHODS

(71) Applicant: Blue Ocean Spine GmbH, Tuttlingen (DE)

(72) Inventors: Guntmar Eisen, Tuttlingen (DE); Markus Salvermoser, Tuttlingen-Möhringen (DE); Jacob Richter, Tuttlingen (DE)

(73) Assignee: Blue Ocean Spine GmbH (DE)

( * ) Notice: Subject to any disclaimer, the term of this patent is extended or adjusted under 35 U.S.C. 154(b) by 65 days.

(21) Appl. No.: 17/865,755

(22) Filed: Jul. 15, 2022

(65) Prior Publication Data
US 2023/0023033 A1    Jan. 26, 2023

Related U.S. Application Data

(60) Provisional application No. 63/222,498, filed on Jul. 16, 2021, provisional application No. 63/222,506, (Continued)

(51) Int. Cl.
*A61F 2/44*        (2006.01)
*A61B 17/88*       (2006.01)
(Continued)

(52) U.S. Cl.
CPC .......... *A61F 2/4455* (2013.01); *A61F 2/4611* (2013.01); *A61F 2002/30471* (2013.01);
(Continued)

(58) Field of Classification Search
CPC ............................ A61F 2/4455–2/447; A61F 2250/0004–2250/001; A61F 2250/0048
(Continued)

(56) References Cited

U.S. PATENT DOCUMENTS 5,676,702 A    10/1997   Ratron
6,102,950 A    8/2000    Vaccaro
(Continued)

FOREIGN PATENT DOCUMENTS

AU    2015268677 A1    6/2016
DE    10307758 B4      2/2005
(Continued)

OTHER PUBLICATIONS

US 10,940,020 B2, 03/2021, Branch et al. (withdrawn)
(Continued)

*Primary Examiner* — Eduardo C Robert
*Assistant Examiner* — David C Comstock
(74) *Attorney, Agent, or Firm* — Farber LLC

(57) ABSTRACT

The present disclosure provides adjustable spinal devices, instruments for implanting the spinal devices, methods for adjusting the height and/or lordosis angles of the spinal devices and methods for implanting such devices. An adjustable spinal fusion device includes an upper plate having an outer surface for placement against a first vertebral body and a lower plate having an outer surface for placement against a second vertebral body. The device further includes a translation member configured to move longitudinally relative to the upper and lower plates to adjust an angle between the upper and lower plates. The translation member may include an angled surface or wedge for cooperating with a ramp on the device to pivot the proximal end of the upper endplate relative to the proximal end of the lower endplate and thereby adjust a distance between the distal ends of the endplates.

8 Claims, 25 Drawing Sheets

Related U.S. Application Data filed on Jul. 16, 2021, provisional application No. 63/222,482, filed on Jul. 16, 2021.

(51) Int. Cl.
*A61F 2/46* (2006.01)
*A61F 2/30* (2006.01)

(52) U.S. Cl.
CPC ............... *A61F 2002/3054* (2013.01); *A61F 2002/30579* (2013.01); *A61F 2002/4627* (2013.01)

(58) Field of Classification Search
USPC .......... 623/17.11, 17.15, 17.16; 606/246, 99, 606/86 A
See application file for complete search history.

(56) References Cited

U.S. PATENT DOCUMENTS

| | | | |
|---|---|---|---|
| 6,126,689 A | 10/2000 | Brett | |
| 6,179,873 B1 | 1/2001 | Zientek | |
| 6,395,031 B1 | 5/2002 | Foley et al. | |
| 6,409,766 B1 | 6/2002 | Brett | |
| 6,767,367 B1 | 7/2004 | Michelson | |
| 6,770,096 B2 | 8/2004 | Bolger et al. | |
| 6,852,129 B2 | 2/2005 | Gerbec et al. | |
| 6,905,512 B2 | 6/2005 | Paes et al. | |
| 6,953,477 B2 | 10/2005 | Berry | |
| 6,955,691 B2 | 10/2005 | Chae et al. | |
| 6,981,975 B2 | 1/2006 | Michelson | |
| 7,029,498 B2 | 4/2006 | Boehm et al. | |
| 7,094,257 B2 | 8/2006 | Mujwid et al. | |
| 7,112,206 B2 | 9/2006 | Michelson | |
| 7,267,689 B2 | 9/2007 | Kohrs et al. | |
| 7,431,735 B2 | 10/2008 | Liu | |
| 7,547,308 B2 | 6/2009 | Bertagnoli et al. | |
| 7,655,042 B2 | 2/2010 | Foley et al. | |
| 7,708,778 B2 | 5/2010 | Gordon et al. | |
| 7,727,280 B2 | 6/2010 | McLuen | |
| 7,780,675 B2 | 8/2010 | Schneid | |
| 7,828,849 B2 | 11/2010 | Lim | |
| 7,951,199 B2 | 5/2011 | Miller | |
| 7,972,365 B2 | 7/2011 | Michelson | |
| 8,025,665 B2 | 9/2011 | Lim et al. | |
| 8,062,373 B2 | 11/2011 | Fabian, Jr. | |
| 8,062,374 B2 | 11/2011 | Markworth et al. | |
| 8,080,062 B2 | 12/2011 | Armstrong et al. | |
| 8,110,004 B2 | 2/2012 | Valdevit et al. | |
| 8,167,950 B2 | 5/2012 | Aferson et al. | |
| 8,187,332 B2 | 5/2012 | McLuen | |
| 8,206,399 B2 | 6/2012 | Gill et al. | |
| 8,206,449 B2 | 6/2012 | Jansen et al. | |
| 8,221,501 B2 | 7/2012 | Eisermann et al. | |
| 8,221,502 B2 | 7/2012 | Branch, Jr. | |
| 8,241,358 B2 | 8/2012 | Butler et al. | |
| 8,246,686 B1 | 8/2012 | Curran et al. | |
| 8,273,125 B2 | 9/2012 | Baccelli et al. | |
| 8,287,572 B2 | 10/2012 | Bae et al. | |
| 8,292,958 B1 | 10/2012 | Bruffey et al. | |
| 8,303,658 B2 | 11/2012 | Peterman | |
| 8,349,014 B2 | 1/2013 | Barreiro et al. | |
| 8,349,015 B2 | 1/2013 | Bae et al. | |
| 8,361,148 B2 | 1/2013 | Malberg et al. | |
| 8,366,774 B1 | 2/2013 | Bruffey et al. | |
| 8,377,071 B2 | 2/2013 | Lim et al. | |
| 8,382,768 B2 | 2/2013 | Berry et al. | |
| 8,382,842 B2 | 2/2013 | Greenhalgh et al. | |
| 8,394,143 B2 | 3/2013 | Grotz et al. | |
| 8,394,145 B2 | 3/2013 | Weiman | |
| 8,398,713 B2 | 3/2013 | Weiman | |
| 8,403,990 B2 | 3/2013 | Dryer et al. | |
| 8,409,291 B2 | 4/2013 | Blackwell et al. | |
| 8,425,528 B2 | 4/2013 | Berry et al. | |
| 8,435,296 B2 | 5/2013 | Kadaba et al. | |
| 8,435,298 B2 | 5/2013 | Weiman | |
| 8,449,554 B2 | 5/2013 | McClintock | |
| 8,454,695 B2 | 6/2013 | Grotz et al. | |
| 8,460,385 B1 | 6/2013 | Wensel | |
| 8,480,748 B2 | 7/2013 | Poulos | |
| 8,486,147 B2 | 7/2013 | De Villiers et al. | |
| 8,486,149 B2 | 7/2013 | Saidha et al. | |
| 8,491,659 B2 | 7/2013 | Weiman | |
| 8,496,706 B2 | 7/2013 | Ragab et al. | |
| 8,506,635 B2 | 8/2013 | Palmatier et al. | |
| 8,512,348 B2 | 8/2013 | Chabansky et al. | |
| 8,518,120 B2 | 8/2013 | Glerum et al. | |
| 8,523,944 B2 | 9/2013 | Jimenez et al. | |
| 8,523,945 B1 | 9/2013 | Wensel | |
| 8,540,452 B2 | 9/2013 | Jimenez et al. | |
| 8,545,562 B1 | 10/2013 | Materna et al. | |
| 8,545,563 B2 | 10/2013 | Brun et al. | |
| 8,574,299 B2 | 11/2013 | Barreiro et al. | |
| 8,579,907 B2 | 11/2013 | Lim et al. | |
| 8,579,981 B2 | 11/2013 | Lim et al. | |
| 8,579,982 B2 | 11/2013 | Michelson | |
| 8,597,353 B2 | 12/2013 | Kana et al. | |
| 8,603,170 B2 | 12/2013 | Cipoletti et al. | |
| 8,617,245 B2 | 12/2013 | Brett | |
| 8,617,247 B2 | 12/2013 | Lechmann et al. | |
| 8,628,576 B2 | 1/2014 | Triplett et al. | |
| 8,628,577 B1 | 1/2014 | Jimenez | |
| 8,632,595 B2 | 1/2014 | Weiman | |
| 8,641,766 B2 | 2/2014 | Donner et al. | |
| 8,663,329 B2 | 3/2014 | Ernst | |
| 8,663,331 B2 | 3/2014 | McClellan, III et al. | |
| 8,663,332 B1 | 3/2014 | To et al. | |
| 8,685,095 B2 | 4/2014 | Miller et al. | |
| 8,685,098 B2 | 4/2014 | Glerum et al. | |
| 8,685,104 B2 | 4/2014 | Lee et al. | |
| 8,709,086 B2 | 4/2014 | Glerum | |
| 8,715,350 B2 | 5/2014 | Janowski et al. | |
| 8,778,025 B2 | 7/2014 | Ragab et al. | |
| 8,778,027 B2 | 7/2014 | Medina | |
| 8,795,366 B2 | 8/2014 | Varela | |
| 8,801,721 B2 | 8/2014 | Berry et al. | |
| 8,801,792 B2 | 8/2014 | De Villiers et al. | |
| 8,845,731 B2 | 9/2014 | Weiman | |
| 8,845,732 B2 | 9/2014 | Weiman | |
| 8,845,733 B2 | 9/2014 | O'Neil et al. | |
| 8,845,734 B2 | 9/2014 | Weiman | |
| 8,845,738 B2 | 9/2014 | Michelson | |
| 8,852,279 B2 | 10/2014 | Weiman | |
| 8,858,564 B2 | 10/2014 | Errico et al. | |
| 8,876,829 B2 | 11/2014 | Lee | |
| 8,888,853 B2 | 11/2014 | Glerum et al. | |
| 8,888,854 B2 | 11/2014 | Glerum et al. | |
| 8,894,711 B2 | 11/2014 | Varela | |
| 8,894,712 B2 | 11/2014 | Varela | |
| 8,906,100 B2 | 12/2014 | Jimenez et al. | |
| 8,906,101 B2 | 12/2014 | Lee et al. | |
| 8,920,505 B2 | 12/2014 | Aferson et al. | |
| 8,926,704 B2 | 1/2015 | Glerum et al. | |
| 8,940,052 B2 | 1/2015 | Lechmann et al. | |
| 8,956,413 B2 | 2/2015 | Ashley et al. | |
| 8,968,405 B2 | 3/2015 | Kirwan et al. | |
| 8,979,933 B2 | 3/2015 | Vishnubholta et al. | |
| 8,986,389 B2 | 3/2015 | Lim et al. | |
| 8,998,920 B2 | 4/2015 | Berry et al. | |
| 9,005,291 B2 | 4/2015 | Loebl et al. | |
| 9,034,045 B2 | 5/2015 | Davenport et al. | |
| 9,039,771 B2 | 5/2015 | Glerum et al. | |
| 9,044,337 B2 | 6/2015 | Dinville et al. | |
| 9,050,194 B2 | 6/2015 | Thibodeau | |
| 9,066,810 B2 | 6/2015 | Hasse et al. | |
| 9,066,813 B2 | 6/2015 | Farris et al. | |
| 9,101,489 B2 | 8/2015 | Protopsaltis et al. | |
| 9,101,493 B2 | 8/2015 | Trudeau et al. | |
| 9,107,761 B2 | 8/2015 | Lee et al. | |
| 9,119,726 B2 | 9/2015 | Wei | |
| 9,119,730 B2 | 9/2015 | Glerum et al. | |
| 9,125,757 B2 | 9/2015 | Weiman | |
| 9,138,275 B2 | 9/2015 | Bae et al. | |
| 9,138,276 B2 | 9/2015 | Bae et al. | |

(56) References Cited

U.S. PATENT DOCUMENTS

| | | |
|---|---|---|
| 9,138,328 B2 | 9/2015 | Butler et al. |
| 9,173,749 B2 | 11/2015 | Jacofsky et al. |
| 9,186,258 B2 | 11/2015 | Davenport et al. |
| 9,204,974 B2 | 12/2015 | Glerum et al. |
| 9,211,195 B2 | 12/2015 | Poulos |
| 9,211,196 B2 | 12/2015 | Glerum et al. |
| 9,220,606 B2 | 12/2015 | Janowski et al. |
| 9,226,836 B2 | 1/2016 | Glerum |
| 9,233,007 B2 | 1/2016 | Sungarian et al. |
| 9,233,009 B2 | 1/2016 | Gray et al. |
| 9,259,328 B2 | 2/2016 | Pabst et al. |
| 9,271,777 B2 | 3/2016 | Nichols et al. |
| 9,271,846 B2 | 3/2016 | Lim et al. |
| 9,308,099 B2 | 4/2016 | Triplett et al. |
| 9,314,348 B2 | 4/2016 | Emstad |
| 9,320,610 B2 | 4/2016 | Alheidt et al. |
| 9,333,092 B2 | 5/2016 | To et al. |
| 9,345,588 B2 | 5/2016 | Himmelberger et al. |
| 9,351,847 B2 | 5/2016 | Reed et al. |
| 9,351,848 B2 | 5/2016 | Glerum et al. |
| 9,358,123 B2 | 6/2016 | McLuen et al. |
| 9,358,128 B2 | 6/2016 | Glerum et al. |
| 9,358,129 B2 | 6/2016 | Weiman |
| 9,358,131 B2 | 6/2016 | Lorio et al. |
| 9,370,433 B1 | 6/2016 | Morris et al. |
| 9,370,434 B2 | 6/2016 | Weiman |
| 9,381,092 B2 | 7/2016 | Jimenez et al. |
| 9,393,130 B2 | 7/2016 | Suddaby et al. |
| 9,402,733 B1 | 8/2016 | To et al. |
| 9,408,708 B2 | 8/2016 | Greenhalgh |
| 9,408,710 B2 | 8/2016 | Purcell et al. |
| 9,414,936 B2 | 8/2016 | Miller et al. |
| 9,421,110 B2 | 8/2016 | Masson et al. |
| 9,439,771 B2 | 9/2016 | Packer et al. |
| 9,445,913 B2 | 9/2016 | Donner et al. |
| 9,445,917 B2 | 9/2016 | Jimenez et al. |
| 9,445,920 B2 | 9/2016 | Baynham |
| 9,452,063 B2 | 9/2016 | Glerum et al. |
| 9,456,903 B2 | 10/2016 | Glerum et al. |
| 9,456,906 B2 | 10/2016 | Gray et al. |
| 9,463,091 B2 | 10/2016 | Brett |
| 9,463,099 B2 | 10/2016 | Levy et al. |
| 9,474,622 B2 | 10/2016 | McLaughlin et al. |
| 9,474,625 B2 | 10/2016 | Weiman |
| 9,480,573 B2 | 11/2016 | Perloff et al. |
| 9,480,579 B2 | 11/2016 | Davenport et al. |
| 9,486,325 B2 | 11/2016 | Davenport et al. |
| 9,492,285 B2 | 11/2016 | Saidha et al. |
| 9,492,287 B2 | 11/2016 | Glerum et al. |
| 9,492,288 B2 | 11/2016 | Wagner et al. |
| 9,492,289 B2 | 11/2016 | Davenport et al. |
| 9,498,349 B2 | 11/2016 | Patterson et al. |
| 9,498,350 B2 | 11/2016 | Theofilos et al. |
| 9,510,954 B2 | 12/2016 | Glerum et al. |
| 9,510,955 B2 | 12/2016 | Marino et al. |
| 9,539,108 B2 | 1/2017 | Glerum et al. |
| 9,554,918 B2 | 1/2017 | Weiman |
| 9,561,117 B2 | 2/2017 | Lechmann et al. |
| 9,566,163 B2 | 2/2017 | Suddaby et al. |
| 9,572,677 B2 | 2/2017 | Davenport et al. |
| 9,572,685 B2 | 2/2017 | Perry |
| 9,585,766 B2 | 3/2017 | Robinson |
| 9,597,200 B2 | 3/2017 | Glerum et al. |
| 9,603,715 B2 | 3/2017 | Thibodeau |
| 9,603,717 B2 | 3/2017 | Ibarra et al. |
| 9,610,172 B2 | 4/2017 | Butler et al. |
| 9,622,876 B1 | 4/2017 | Greenhalgh et al. |
| 9,642,720 B2 | 5/2017 | Radcliffe et al. |
| 9,642,721 B2 | 5/2017 | Patterson et al. |
| 9,655,737 B2 | 5/2017 | Perloff et al. |
| 9,655,740 B1 | 5/2017 | Faulkner et al. |
| 9,655,747 B2 | 5/2017 | Glerum et al. |
| 9,662,224 B2 | 5/2017 | Weiman et al. |
| 9,687,359 B2 | 6/2017 | Perrow |
| 9,693,876 B1 | 7/2017 | Mesiwala |
| 9,700,430 B2 | 7/2017 | Perrow |
| 9,707,092 B2 | 7/2017 | Davenport et al. |
| 9,707,095 B2 | 7/2017 | Emstad |
| 9,707,099 B2 | 7/2017 | Schiffman et al. |
| 9,707,100 B2 | 7/2017 | Duffield et al. |
| 9,717,600 B1 | 8/2017 | Wensel |
| 9,730,802 B1 | 8/2017 | Harvey |
| 9,737,412 B2 | 8/2017 | Brett |
| 9,750,616 B2 | 9/2017 | Blain et al. |
| 9,750,617 B2 | 9/2017 | Lim et al. |
| 9,750,618 B1 | 9/2017 | Daffinson et al. |
| 9,757,249 B2 | 9/2017 | Radcliffe et al. |
| 9,757,252 B2 | 9/2017 | Lee et al. |
| 9,763,803 B2 | 9/2017 | Dinville et al. |
| 9,770,343 B2 | 9/2017 | Weiman |
| 9,802,297 B2 | 10/2017 | Marchand |
| 9,808,353 B2 | 11/2017 | Suddaby et al. |
| 9,820,866 B2 | 11/2017 | Whipple |
| 9,827,107 B1 | 11/2017 | Arnin |
| 9,833,336 B2 | 12/2017 | Davenport et al. |
| 9,844,445 B2 | 12/2017 | McManus et al. |
| 9,848,997 B2 | 12/2017 | Glerum et al. |
| 9,855,151 B2 | 1/2018 | Weiman |
| 9,861,497 B2 | 1/2018 | Baynham |
| 9,867,715 B2 | 1/2018 | McLaughlin et al. |
| 9,872,779 B2 | 1/2018 | Miller et al. |
| 9,889,019 B2 | 2/2018 | Rogers et al. |
| 9,901,459 B2 | 2/2018 | Faulhaber |
| 9,907,673 B2 | 3/2018 | Weiman et al. |
| 9,913,726 B2 | 3/2018 | Weiman |
| 9,925,062 B2 | 3/2018 | Glerum et al. |
| 9,931,222 B2 | 4/2018 | Grotz et al. |
| 9,937,052 B2 | 4/2018 | Abdou et al. |
| 9,943,418 B2 | 4/2018 | Davenport et al. |
| 9,949,841 B2 | 4/2018 | Glerum et al. |
| 9,949,846 B2 | 4/2018 | Duffield et al. |
| 9,956,087 B2 | 5/2018 | Seifert et al. |
| 9,962,270 B2 | 5/2018 | Alheidt et al. |
| 9,962,271 B2 | 5/2018 | Glerum |
| 9,962,272 B1 | 5/2018 | Daffinson et al. |
| 9,968,462 B2 | 5/2018 | Weiman |
| 9,974,662 B2 | 5/2018 | Hessler et al. |
| 9,974,664 B2 | 5/2018 | Emerick et al. |
| 9,980,822 B2 | 5/2018 | Perloff et al. |
| 9,987,142 B2 | 6/2018 | McConnell |
| 9,987,146 B1 | 6/2018 | Lentner et al. |
| 9,999,517 B2 | 6/2018 | To et al. |
| 10,010,430 B2 | 7/2018 | Glerum et al. |
| 10,016,282 B2 | 7/2018 | Seifert et al. |
| 10,022,239 B1 | 7/2018 | Lentner et al. |
| 10,022,241 B2 | 7/2018 | Faulhaber et al. |
| 10,022,245 B2 | 7/2018 | Frasier et al. |
| 10,028,842 B2 | 7/2018 | Gray et al. |
| 10,034,765 B2 | 7/2018 | Blain et al. |
| 10,034,769 B2 | 7/2018 | Baynham |
| 10,034,772 B2 | 7/2018 | Glerum et al. |
| 10,034,773 B2 | 7/2018 | McLaughlin et al. |
| 10,052,213 B2 | 8/2018 | Glerum et al. |
| 10,052,215 B2 | 8/2018 | Hessler et al. |
| 10,058,433 B2 | 8/2018 | Lechmann et al. |
| 10,058,435 B2 | 8/2018 | Lee et al. |
| 10,060,469 B2 | 8/2018 | Jimenez et al. |
| 10,070,971 B2 | 9/2018 | Palmatier et al. |
| 10,076,421 B2 | 9/2018 | Dewey |
| 10,080,666 B2 | 9/2018 | Suddaby et al. |
| 10,080,669 B2 | 9/2018 | Davenport et al. |
| 10,092,422 B2 | 10/2018 | McLuen et al. |
| 10,098,755 B2 | 10/2018 | Kaufmann et al. |
| 10,098,756 B2 | 10/2018 | Emstad |
| 10,098,757 B2 | 10/2018 | Logan et al. |
| 10,098,758 B2 | 10/2018 | Matthews et al. |
| 10,098,759 B2 | 10/2018 | Weiman |
| 10,105,236 B2 | 10/2018 | Donner et al. |
| 10,105,238 B2 | 10/2018 | Koch et al. |
| 10,137,001 B2 | 11/2018 | Weiman |
| 10,137,007 B2 | 11/2018 | Dewey et al. |
| 10,143,569 B2 | 12/2018 | Weiman et al. |
| 10,149,770 B2 | 12/2018 | Loebl et al. |
| 10,154,912 B2 | 12/2018 | Glerum |

(56) References Cited

U.S. PATENT DOCUMENTS

| | | |
|---|---|---|
| 10,172,718 B2 | 1/2019 | Wolters et al. |
| 10,182,922 B2 | 1/2019 | Nichols et al. |
| 10,188,524 B2 | 1/2019 | Buss |
| 10,188,526 B2 | 1/2019 | Kuyler |
| 10,188,527 B2 | 1/2019 | Rogers et al. |
| 10,195,050 B2 | 2/2019 | Palmatier et al. |
| 10,206,788 B2 | 2/2019 | Field et al. |
| 10,219,913 B2 | 3/2019 | Matthews et al. |
| 10,219,914 B2 | 3/2019 | Faulhaber |
| 10,219,916 B2 | 3/2019 | Tanaka et al. |
| 10,226,355 B2 | 3/2019 | Zeegers |
| 10,226,359 B2 | 3/2019 | Glerum et al. |
| 10,238,503 B2 | 3/2019 | Branch et al. |
| 10,265,191 B2 | 4/2019 | Lim et al. |
| 10,265,192 B2 | 4/2019 | Eastlack et al. |
| 10,271,959 B2 | 4/2019 | Bae et al. |
| 10,271,961 B2 | 4/2019 | Aferzon et al. |
| 10,278,830 B1 | 5/2019 | Walker et al. |
| 10,278,831 B2 | 5/2019 | Sandul |
| 10,285,820 B2 | 5/2019 | Greenhalgh |
| 10,292,828 B2 | 5/2019 | Greenhalgh |
| 10,292,830 B2 | 5/2019 | McLuen et al. |
| 10,292,835 B2 | 5/2019 | Barreiro et al. |
| 10,307,265 B2 | 6/2019 | Sack |
| 10,314,719 B2 | 6/2019 | Hessler et al. |
| 10,322,007 B2 | 6/2019 | Masson et al. |
| 10,322,010 B2 | 6/2019 | Bannigan |
| 10,327,917 B2 | 6/2019 | Glerum et al. |
| 10,350,081 B2 | 7/2019 | Seifert et al. |
| 10,350,084 B1 | 7/2019 | Lin et al. |
| 10,350,085 B2 | 7/2019 | Glerum et al. |
| 10,363,142 B2 | 7/2019 | McClintock et al. |
| 10,376,378 B2 | 8/2019 | Ashleigh et al. |
| 10,390,962 B2 | 8/2019 | Weiman |
| 10,390,963 B2 | 8/2019 | Olmos et al. |
| 10,398,565 B2 | 9/2019 | Bender et al. |
| 10,398,566 B2 | 9/2019 | Olmos et al. |
| 10,398,567 B2 | 9/2019 | Robinson |
| 10,398,573 B2 | 9/2019 | Duffield et al. |
| 10,405,988 B2 | 9/2019 | Grotz et al. |
| 10,405,992 B2 | 9/2019 | Sack |
| 10,413,419 B2 | 9/2019 | Thibodeau |
| 10,413,422 B2 | 9/2019 | Flower et al. |
| 10,433,975 B2 | 10/2019 | Ashleigh et al. |
| 10,441,430 B2 | 10/2019 | Ludwig et al. |
| 10,441,433 B2 | 10/2019 | Patel et al. |
| 10,449,060 B2 | 10/2019 | Sack |
| 10,485,674 B2 | 11/2019 | Perloff et al. |
| 10,485,675 B2 | 11/2019 | Sharifi-Mehr et al. |
| 10,507,116 B2 | 12/2019 | Shoshtaev |
| 10,512,551 B2 | 12/2019 | Eastlack et al. |
| 10,524,924 B2 | 1/2020 | Davenport et al. |
| 10,524,929 B2 | 1/2020 | Shoshtaev |
| 10,524,930 B2 | 1/2020 | Duffield et al. |
| 10,531,961 B2 | 1/2020 | Dinville et al. |
| 10,531,964 B2 | 1/2020 | Miller et al. |
| 10,543,106 B2 | 1/2020 | Robinson |
| 10,543,108 B2 | 1/2020 | Dvorak et al. |
| 10,548,743 B2 | 2/2020 | Faulhaber |
| 10,568,747 B2 | 2/2020 | Boehm et al. |
| 10,575,960 B2 | 3/2020 | Duffield et al. |
| 10,583,015 B2 | 3/2020 | Olmos et al. |
| 10,610,374 B2 | 4/2020 | Shulock et al. |
| 10,610,376 B2 | 4/2020 | Kuyler et al. |
| 10,610,377 B2 | 4/2020 | Baynham |
| 10,617,530 B2 | 4/2020 | Siegal et al. |
| 10,617,533 B2 | 4/2020 | Glerum et al. |
| 10,631,997 B2 | 4/2020 | Ashleigh et al. |
| 10,639,166 B2 | 5/2020 | Weiman et al. |
| 10,646,351 B2 | 5/2020 | Blain et al. |
| 10,667,922 B2 | 6/2020 | Saidha et al. |
| 10,667,925 B2 | 6/2020 | Emerick et al. |
| 10,667,927 B2 | 6/2020 | Lamborne et al. |
| 10,682,239 B2 | 6/2020 | Hsu et al. |
| 10,682,241 B2 | 6/2020 | Glerum et al. |
| 10,702,391 B2 | 7/2020 | Ameil et al. |
| 10,702,392 B2 | 7/2020 | Greenhalgh |
| 10,702,393 B2 | 7/2020 | Davenport et al. |
| 10,702,396 B2 | 7/2020 | Burrows-Ownbey et al. |
| 10,709,571 B2 | 7/2020 | Iott et al. |
| 10,709,573 B2 | 7/2020 | Weiman et al. |
| 10,709,575 B2 | 7/2020 | Robinson |
| 10,722,377 B2 | 7/2020 | Glerum et al. |
| 10,722,379 B2 | 7/2020 | McLaughlin et al. |
| 10,722,380 B1 | 7/2020 | Berry |
| 10,729,553 B2 | 8/2020 | Bell et al. |
| 10,729,561 B2 | 8/2020 | Glerum |
| 10,744,002 B2 | 8/2020 | Glerum et al. |
| 10,751,187 B2 | 8/2020 | Allain et al. |
| 10,758,368 B2 | 9/2020 | To et al. |
| 10,758,369 B2 | 9/2020 | Rogers et al. |
| 10,758,370 B2 | 9/2020 | Gilbride et al. |
| 10,758,371 B2 | 9/2020 | Hessler et al. |
| 10,765,528 B2 | 9/2020 | Weiman et al. |
| 10,765,532 B2 | 9/2020 | Ashleigh et al. |
| 10,772,737 B2 | 9/2020 | Gray et al. |
| 10,779,955 B2 | 9/2020 | Kuyler et al. |
| 10,779,956 B2 | 9/2020 | Perrow |
| 10,779,957 B2 | 9/2020 | Weiman et al. |
| 10,786,364 B2 | 9/2020 | Davenport et al. |
| 10,786,366 B2 | 9/2020 | To et al. |
| 10,786,367 B2 | 9/2020 | Sharabani |
| 10,786,368 B2 | 9/2020 | Riemhofer et al. |
| 10,799,368 B2 | 10/2020 | Glerum et al. |
| 10,806,592 B2 | 10/2020 | Donner et al. |
| 10,835,389 B2 | 11/2020 | Errico et al. |
| 10,842,633 B2 | 11/2020 | Predick et al. |
| 10,842,640 B2 | 11/2020 | Weiman et al. |
| 10,842,641 B2 | 11/2020 | Sharabani et al. |
| 10,842,643 B2 | 11/2020 | Farris et al. |
| 10,842,649 B2 | 11/2020 | Rogers et al. |
| 10,856,997 B2 | 12/2020 | Cowan et al. |
| 10,864,086 B2 | 12/2020 | Weiman |
| 10,864,087 B2 | 12/2020 | Faulhaber et al. |
| 10,869,768 B2 | 12/2020 | Weiman et al. |
| 10,869,769 B2 | 12/2020 | Eisen et al. |
| 10,874,522 B2 | 12/2020 | Weiman |
| 10,874,523 B2 | 12/2020 | Weiman et al. |
| 10,874,524 B2 | 12/2020 | Bjork |
| 10,881,524 B2 | 1/2021 | Eisen et al. |
| 10,881,531 B2 | 1/2021 | Berry |
| 10,888,433 B2 | 1/2021 | Frasier et al. |
| 10,888,434 B2 | 1/2021 | Adamo et al. |
| 10,888,435 B2 | 1/2021 | Adamo et al. |
| 10,898,344 B2 | 1/2021 | Alheidt et al. |
| 10,925,747 B2 | 2/2021 | Bae et al. |
| 10,925,748 B2 | 2/2021 | Grim et al. |
| 10,925,752 B2 | 2/2021 | Weiman |
| 10,932,920 B2 | 3/2021 | Dewey et al. |
| 10,940,014 B2 | 3/2021 | Greenhalgh |
| 10,940,016 B2 | 3/2021 | Thommen et al. |
| 10,940,018 B2 | 3/2021 | Sharifi-Mehr et al. |
| 10,940,025 B2 | 3/2021 | O'Neil et al. |
| 10,945,725 B2 | 3/2021 | Hollis et al. |
| 10,945,857 B2 | 3/2021 | Emstad |
| 10,945,859 B2 | 3/2021 | Ewer et al. |
| 10,959,856 B2 | 3/2021 | Seifert et al. |
| 10,973,648 B1 | 4/2021 | Abdou |
| 10,973,649 B2 | 4/2021 | Weiman et al. |
| 10,973,650 B2 | 4/2021 | Stein |
| 10,973,652 B2 | 4/2021 | Hawkins et al. |
| 10,980,589 B2 | 4/2021 | Defalco et al. |
| 10,980,642 B2 | 4/2021 | Glerum et al. |
| 10,980,644 B2 | 4/2021 | Purcell et al. |
| 10,987,233 B2 | 4/2021 | Siccardi et al. |
| 10,993,757 B2 | 5/2021 | Schifano et al. |
| 10,993,814 B2 | 5/2021 | Wolters |
| 10,993,815 B2 | 5/2021 | Ewer et al. |
| 10,993,816 B2 | 5/2021 | Kieser et al. |
| 11,000,385 B2 | 5/2021 | Kalhorn et al. |
| 11,007,067 B2 | 5/2021 | Masson et al. |
| 11,013,610 B2 | 5/2021 | Vigliotti et al. |
| 11,013,614 B2 | 5/2021 | Barreiro et al. |
| 11,013,617 B2 | 5/2021 | Weiman et al. |

(56) References Cited

U.S. PATENT DOCUMENTS

| | | |
|---|---|---|
| 11,020,238 B2 | 6/2021 | Nichols et al. |
| 11,020,239 B2 | 6/2021 | Miller et al. |
| 11,020,241 B2 | 6/2021 | Predick |
| 11,026,800 B2 | 6/2021 | Seifert et al. |
| 11,026,804 B2 | 6/2021 | Jimenez et al. |
| 11,033,401 B2 | 6/2021 | Shoshtaev |
| 11,033,402 B2 | 6/2021 | Melkent et al. |
| 11,033,403 B2 | 6/2021 | Predick et al. |
| 11,033,404 B2 | 6/2021 | Faulhaber |
| 11,045,325 B2 | 6/2021 | Bernard et al. |
| 11,045,326 B2 | 6/2021 | Seifert et al. |
| 2006/0122701 A1 | 6/2006 | Kiester |
| 2008/0281346 A1 | 11/2008 | Greenhalgh |
| 2009/0281629 A1 | 11/2009 | Roebling et al. |
| 2012/0029644 A1 | 2/2012 | Markworth et al. |
| 2012/0078371 A1 | 3/2012 | Gamache et al. |
| 2012/0095559 A1 | 4/2012 | Woods et al. |
| 2013/0085572 A1 | 4/2013 | Glerum et al. |
| 2013/0116791 A1 | 5/2013 | Theofilos |
| 2014/0094917 A1 | 4/2014 | Salerni |
| 2014/0172104 A1 | 6/2014 | Dugal et al. |
| 2014/0194992 A1 | 7/2014 | Medina |
| 2014/0277501 A1 | 9/2014 | Northcutt et al. |
| 2014/0379085 A1 | 12/2014 | Duffield et al. |
| 2015/0100128 A1 | 4/2015 | Glerum et al. |
| 2015/0182347 A1* | 7/2015 | Robinson ............ A61F 2/447 623/17.15 |
| 2015/0230931 A1 | 8/2015 | Greenhalgh |
| 2015/0305880 A1 | 10/2015 | Kim et al. |
| 2016/0095717 A1 | 4/2016 | Poulos |
| 2016/0151169 A1 | 6/2016 | Hawkins et al. |
| 2016/0256291 A1 | 9/2016 | Miller |
| 2016/0310291 A1 | 10/2016 | Greenhalgh |
| 2017/0042695 A1 | 2/2017 | Foley et al. |
| 2017/0056179 A1 | 3/2017 | Lorio |
| 2017/0100255 A1 | 4/2017 | Hleihil et al. |
| 2017/0100257 A1 | 4/2017 | Weiman et al. |
| 2017/0112630 A1* | 4/2017 | Kuyler ............ A61F 2/4455 |
| 2017/0119538 A1 | 5/2017 | Baynham |
| 2017/0165082 A1 | 6/2017 | Faulhaber |
| 2017/0181863 A1 | 6/2017 | Bjork |
| 2017/0231780 A1 | 8/2017 | D'Urso |
| 2017/0239063 A1 | 8/2017 | Predick |
| 2017/0281358 A1 | 10/2017 | Wagner et al. |
| 2017/0290677 A1 | 10/2017 | Olmos et al. |
| 2017/0319353 A1 | 11/2017 | Greenhalgh et al. |
| 2017/0333198 A1 | 11/2017 | Robinson |
| 2017/0333199 A1 | 11/2017 | Sharifi-Mehr et al. |
| 2017/0333200 A1* | 11/2017 | Arnin ............ A61F 2/4455 |
| 2017/0348115 A1 | 12/2017 | Greenhalgh et al. |
| 2017/0348116 A1 | 12/2017 | Weiman |
| 2017/0367844 A1 | 12/2017 | Eisen et al. |
| 2017/0367845 A1 | 12/2017 | Eisen et al. |
| 2018/0064554 A1 | 3/2018 | Brett |
| 2018/0064555 A1 | 3/2018 | Poulos |
| 2018/0092753 A1 | 4/2018 | Dinville et al. |
| 2018/0116815 A1* | 5/2018 | Kuyler ............ A61F 2/4611 |
| 2018/0161175 A1 | 6/2018 | Frasier et al. |
| 2018/0177603 A1 | 6/2018 | Weiman et al. |
| 2018/0185163 A1 | 7/2018 | Weiman et al. |
| 2018/0193164 A1 | 7/2018 | Shoshtaev |
| 2018/0207003 A1 | 7/2018 | Melkent et al. |
| 2018/0256359 A1 | 9/2018 | Greenhalgh |
| 2018/0303621 A1 | 10/2018 | Brotman et al. |
| 2018/0303625 A1 | 10/2018 | Alheidt et al. |
| 2018/0311048 A1 | 11/2018 | Glerum et al. |
| 2018/0318101 A1 | 11/2018 | Engstrom |
| 2018/0325693 A1 | 11/2018 | Weiman et al. |
| 2018/0338838 A1 | 11/2018 | Cryder et al. |
| 2018/0344476 A1 | 12/2018 | Koch |
| 2018/0360616 A1 | 12/2018 | Luu |
| 2018/0368987 A9 | 12/2018 | Davis et al. |
| 2019/0000640 A1 | 1/2019 | Weiman |
| 2019/0008654 A1 | 1/2019 | Thommen et al. |
| 2019/0021868 A1 | 1/2019 | Ludwig et al. |
| 2019/0060083 A1 | 2/2019 | Weiman et al. |
| 2019/0076263 A1 | 3/2019 | Emstad |
| 2019/0091033 A1 | 3/2019 | Dewey et al. |
| 2019/0091034 A1 | 3/2019 | Dewey et al. |
| 2019/0091036 A1 | 3/2019 | Levy et al. |
| 2019/0105174 A1 | 4/2019 | Kaufmann et al. |
| 2019/0110900 A1 | 4/2019 | Suddaby |
| 2019/0110902 A1 | 4/2019 | Vigliotti et al. |
| 2019/0133780 A1 | 5/2019 | Matthews et al. |
| 2019/0133784 A1 | 5/2019 | Gunn et al. |
| 2019/0151111 A1* | 5/2019 | Dewey ............ A61F 2/447 |
| 2019/0151115 A1 | 5/2019 | Nichols et al. |
| 2019/0168115 A1 | 6/2019 | Deridder et al. |
| 2019/0183656 A1 | 6/2019 | Stein |
| 2019/0201209 A1 | 7/2019 | Branch et al. |
| 2019/0201210 A1 | 7/2019 | Besaw et al. |
| 2019/0224017 A1 | 7/2019 | Grim et al. |
| 2019/0224021 A1 | 7/2019 | Bae et al. |
| 2019/0231548 A1 | 8/2019 | Ewer et al. |
| 2019/0231552 A1 | 8/2019 | Sandul |
| 2019/0240039 A1 | 8/2019 | Walker et al. |
| 2019/0240043 A1 | 8/2019 | Greenhalgh |
| 2019/0254836 A1 | 8/2019 | Cowan et al. |
| 2019/0254839 A1 | 8/2019 | Nichols et al. |
| 2019/0262139 A1 | 8/2019 | Wolters |
| 2019/0262140 A1 | 8/2019 | Bannigan |
| 2019/0262141 A1 | 8/2019 | Barreiro et al. |
| 2019/0269521 A1 | 9/2019 | Shoshtaev |
| 2019/0271997 A1 | 9/2019 | Harvey |
| 2019/0274836 A1 | 9/2019 | Eisen et al. |
| 2019/0274837 A1 | 9/2019 | Eisen et al. |
| 2019/0274841 A1 | 9/2019 | Hawkes et al. |
| 2019/0274845 A1 | 9/2019 | Ludwig et al. |
| 2019/0282372 A1 | 9/2019 | Sack |
| 2019/0282373 A1 | 9/2019 | Alheidt |
| 2019/0290446 A1 | 9/2019 | Masson et al. |
| 2019/0290448 A1 | 9/2019 | Predick et al. |
| 2019/0298524 A1 | 10/2019 | Lauf et al. |
| 2019/0298540 A1 | 10/2019 | Aghayev et al. |
| 2019/0307577 A1 | 10/2019 | Predick et al. |
| 2019/0314167 A1 | 10/2019 | Bender et al. |
| 2019/0314168 A1 | 10/2019 | Faulhaber |
| 2019/0321190 A1 | 10/2019 | Wagner et al. |
| 2019/0321191 A1 | 10/2019 | Glerum et al. |
| 2019/0328540 A1 | 10/2019 | Seifert et al. |
| 2019/0328543 A1 | 10/2019 | Lin et al. |
| 2019/0328544 A1 | 10/2019 | Ashley et al. |
| 2019/0336299 A1 | 11/2019 | Bernard et al. |
| 2019/0336300 A1 | 11/2019 | Bernard et al. |
| 2019/0336301 A1 | 11/2019 | Engstrom |
| 2019/0336302 A1 | 11/2019 | Seifert et al. |
| 2019/0336303 A1 | 11/2019 | Ashleigh et al. |
| 2019/0336305 A1 | 11/2019 | Joly et al. |
| 2019/0343654 A1 | 11/2019 | Laurence et al. |
| 2019/0343655 A1 | 11/2019 | Bruffey et al. |
| 2019/0343657 A1 | 11/2019 | Duffield et al. |
| 2019/0358049 A1 | 11/2019 | Faulhaber |
| 2019/0374345 A1 | 12/2019 | Thibodeau |
| 2019/0388231 A1 | 12/2019 | Biedermann et al. |
| 2019/0388232 A1 | 12/2019 | Purcell et al. |
| 2019/0388238 A1 | 12/2019 | Lechmann et al. |
| 2020/0000606 A1 | 1/2020 | Grotz et al. |
| 2020/0000607 A1 | 1/2020 | To et al. |
| 2020/0008951 A1 | 1/2020 | McClintock et al. |
| 2020/0008955 A1 | 1/2020 | Ashleigh et al. |
| 2020/0015986 A1 | 1/2020 | Sack |
| 2020/0030110 A1 | 1/2020 | Sharabani et al. |
| 2020/0046514 A1 | 2/2020 | Gilbride et al. |
| 2020/0046515 A1 | 2/2020 | To et al. |
| 2020/0046516 A1 | 2/2020 | Curran et al. |
| 2020/0046517 A1 | 2/2020 | Perloff et al. |
| 2020/0054455 A1 | 2/2020 | Renani |
| 2020/0054461 A1 | 2/2020 | Marrocco et al. |
| 2020/0054463 A1 | 2/2020 | Himmelberger et al. |
| 2020/0069435 A1 | 3/2020 | Eastlack et al. |
| 2020/0078190 A1 | 3/2020 | Rogers et al. |
| 2020/0085586 A1 | 3/2020 | Ludwig et al. |
| 2020/0093603 A1 | 3/2020 | Manwill et al. |
| 2020/0093607 A1 | 3/2020 | Davenport et al. |

(56) References Cited

U.S. PATENT DOCUMENTS

| | | |
|---|---|---|
| 2020/0093609 A1 | 3/2020 | Shoshtaev |
| 2020/0100905 A1 | 4/2020 | Sharifi-Mehr et al. |
| 2020/0107938 A1 | 4/2020 | Faulhaber |
| 2020/0113708 A1 | 4/2020 | Dinville et al. |
| 2020/0121471 A1 | 4/2020 | Sharifi-Mehr et al. |
| 2020/0129306 A1 | 4/2020 | Miller et al. |
| 2020/0129307 A1 | 4/2020 | Hunziker et al. |
| 2020/0138588 A1 | 5/2020 | Lorio |
| 2020/0138594 A1 | 5/2020 | Renganath et al. |
| 2020/0138595 A1 | 5/2020 | Shoshtaev et al. |
| 2020/0138600 A1 | 5/2020 | Weiman et al. |
| 2020/0146840 A1 | 5/2020 | Black et al. |
| 2020/0146843 A1 | 5/2020 | Faulhaber |
| 2020/0170806 A1 | 6/2020 | Ashleigh et al. |
| 2020/0179135 A1 | 6/2020 | Castro |
| 2020/0188128 A1 | 6/2020 | Sack |
| 2020/0188131 A1 | 6/2020 | McLuen et al. |
| 2020/0205992 A1 | 7/2020 | Bernard et al. |
| 2020/0205993 A1 | 7/2020 | Davenport et al. |
| 2020/0214851 A1 | 7/2020 | Kalhorn et al. |
| 2020/0222202 A1 | 7/2020 | Kuyler et al. |
| 2020/0229936 A1 | 7/2020 | Milz et al. |
| 2020/0229944 A1* | 7/2020 | Suh ................... A61F 2/4455 |
| 2020/0237521 A1 | 7/2020 | Siegal et al. |
| 2020/0237525 A1 | 7/2020 | Weiman et al. |
| 2020/0246159 A1 | 8/2020 | Suh et al. |
| 2020/0253744 A1 | 8/2020 | Saidha et al. |
| 2020/0253746 A1 | 8/2020 | Duffield et al. |
| 2020/0253748 A1 | 8/2020 | McLuen et al. |
| 2020/0261236 A1 | 8/2020 | Prevost et al. |
| 2020/0261238 A1 | 8/2020 | Robinson |
| 2020/0261241 A1 | 8/2020 | Robinson |
| 2020/0268524 A1 | 8/2020 | Glerum et al. |
| 2020/0276028 A1 | 9/2020 | Blain et al. |
| 2020/0281739 A1 | 9/2020 | Jimenez et al. |
| 2020/0281741 A1 | 9/2020 | Grotz |
| 2020/0289289 A1 | 9/2020 | Shulock et al. |
| 2020/0297506 A1 | 9/2020 | Olmos et al. |
| 2020/0297507 A1 | 9/2020 | Iott et al. |
| 2020/0297510 A1 | 9/2020 | Woodruff |
| 2020/0297511 A1 | 9/2020 | Gray et al. |
| 2020/0315679 A1 | 10/2020 | Vrionis et al. |
| 2020/0315811 A1 | 10/2020 | Cryder et al. |
| 2020/0323643 A1 | 10/2020 | Glerum et al. |
| 2020/0330239 A1 | 10/2020 | Davenport et al. |
| 2020/0330240 A1 | 10/2020 | Greenhalgh et al. |
| 2020/0330241 A1 | 10/2020 | Blain et al. |
| 2020/0337854 A1 | 10/2020 | Schmura et al. |
| 2020/0337862 A1 | 10/2020 | Baker et al. |
| 2020/0345511 A1 | 11/2020 | Daffinson et al. |
| 2020/0345512 A1 | 11/2020 | Zakelj |
| 2020/0345513 A1 | 11/2020 | Glerum et al. |
| 2020/0352730 A1 | 11/2020 | Bell et al. |
| 2020/0352732 A1 | 11/2020 | To et al. |
| 2020/0352738 A1 | 11/2020 | Berry |
| 2020/0352740 A1 | 11/2020 | Vazifehdan et al. |
| 2020/0360151 A1 | 11/2020 | Kuyler et al. |
| 2020/0360152 A1 | 11/2020 | Kim et al. |
| 2020/0360153 A1 | 11/2020 | Weiman et al. |
| 2020/0360156 A1 | 11/2020 | Knapp et al. |
| 2020/0368034 A1 | 11/2020 | Etminan |
| 2020/0368035 A1 | 11/2020 | Gilbride et al. |
| 2020/0375751 A1 | 12/2020 | Dinville et al. |
| 2020/0375752 A1 | 12/2020 | Ashleigh et al. |
| 2020/0375753 A1 | 12/2020 | McLaughlin et al. |
| 2020/0375755 A1 | 12/2020 | Cain |
| 2020/0383798 A1 | 12/2020 | Butler et al. |
| 2020/0383799 A1 | 12/2020 | Cain |
| 2020/0390565 A1 | 12/2020 | Jimenez et al. |
| 2020/0397593 A1 | 12/2020 | Davenport et al. |
| 2020/0405497 A1 | 12/2020 | Olmos et al. |
| 2020/0405499 A1 | 12/2020 | Gerbec et al. |
| 2020/0405500 A1 | 12/2020 | Marden et al. |
| 2021/0000160 A1 | 1/2021 | Olmos et al. |
| 2021/0000610 A1 | 1/2021 | Rogers et al. |
| 2021/0007860 A1 | 1/2021 | Glerum et al. |
| 2021/0015627 A1 | 1/2021 | Weiman et al. |
| 2021/0015631 A1 | 1/2021 | Davenport et al. |
| 2021/0022884 A1 | 1/2021 | Oglaza et al. |
| 2021/0030555 A1 | 2/2021 | Weiman et al. |
| 2021/0030556 A1 | 2/2021 | Perrow |
| 2021/0030557 A1 | 2/2021 | Robinson |
| 2021/0030560 A1 | 2/2021 | Abu-Mulaweh et al. |
| 2021/0030561 A1* | 2/2021 | Gleason ................ A61F 2/4611 |
| 2021/0038406 A1 | 2/2021 | Pimenta et al. |
| 2021/0052395 A1 | 2/2021 | Iott et al. |
| 2021/0059839 A1 | 3/2021 | Hessler et al. |
| 2021/0068959 A1 | 3/2021 | McLuen et al. |
| 2021/0068973 A1* | 3/2021 | McLuen ................ A61F 2/447 |
| 2021/0068974 A1 | 3/2021 | Cowan et al. |
| 2021/0068976 A1 | 3/2021 | Predick et al. |
| 2021/0068977 A1 | 3/2021 | Faulhaber |
| 2021/0068982 A1 | 3/2021 | Carnes et al. |
| 2021/0069584 A1 | 3/2021 | Deridder et al. |
| 2021/0077157 A1 | 3/2021 | Bosio et al. |
| 2021/0077272 A1 | 3/2021 | Eisen et al. |
| 2021/0077273 A1 | 3/2021 | Sharabani et al. |
| 2021/0077274 A1 | 3/2021 | Robie |
| 2021/0085485 A1 | 3/2021 | Reimhofer et al. |
| 2021/0085486 A1 | 3/2021 | Burrows-Ownbey et al. |
| 2021/0093463 A1 | 4/2021 | Eisen et al. |
| 2021/0093467 A1 | 4/2021 | Adamo et al. |
| 2021/0106430 A1 | 4/2021 | Mermuys et al. |
| 2021/0106434 A1 | 4/2021 | Alheidt et al. |
| 2021/0113347 A1 | 4/2021 | Fessler et al. |
| 2021/0113348 A1 | 4/2021 | Lopez |
| 2021/0113349 A1 | 4/2021 | Weiman et al. |
| 2021/0113350 A1 | 4/2021 | Adamo et al. |
| 2021/0121299 A1 | 4/2021 | Hyder |
| 2021/0121300 A1 | 4/2021 | Weiman et al. |
| 2021/0128315 A1 | 5/2021 | Predick |
| 2021/0137685 A1 | 5/2021 | Kahmer et al. |
| 2021/0137697 A1 | 5/2021 | Weiman |
| 2021/0137699 A1 | 5/2021 | Jang et al. |
| 2021/0145600 A1 | 5/2021 | Sharifi-Mehr et al. |
| 2021/0145607 A1 | 5/2021 | Kuyler et al. |
| 2021/0154021 A1 | 5/2021 | Bae et al. |
| 2021/0161678 A1 | 6/2021 | Dewey et al. |
| 2021/0161682 A1 | 6/2021 | O'Neil et al. |
| 2021/0169656 A1 | 6/2021 | Hawkins et al. |
| 2021/0169659 A1 | 6/2021 | Grim et al. |
| 2021/0177618 A1 | 6/2021 | Branch et al. |
| 2021/0177619 A1 | 6/2021 | Voellmicke et al. |
| 2021/0186706 A1 | 6/2021 | Spitler et al. |

FOREIGN PATENT DOCUMENTS

| | | |
|---|---|---|
| DE | 102013102955 B4 | 7/2017 |
| DE | 202017105466 U1 | 9/2017 |
| DE | 102018206693 B3 | 2/2019 |
| DE | 102015101675 B4 | 3/2019 |
| EP | 0977529 B1 | 2/2003 |
| EP | 1001722 B1 | 10/2003 |
| EP | 1014899 B1 | 8/2004 |
| EP | 1532949 B1 | 7/2007 |
| EP | 1698305 B1 | 8/2007 |
| EP | 1290985 B1 | 4/2008 |
| EP | 1925272 B1 | 1/2010 |
| EP | 1843723 B1 | 3/2010 |
| EP | 1372540 B1 | 11/2010 |
| EP | 1706075 B1 | 1/2011 |
| EP | 1903994 B9 | 6/2011 |
| EP | 1385457 B1 | 10/2011 |
| EP | 1793768 B1 | 11/2011 |
| EP | 2157938 B1 | 2/2012 |
| EP | 1699389 B1 | 4/2012 |
| EP | 1718216 B1 | 4/2012 |
| EP | 2226039 B1 | 11/2015 |
| EP | 2967659 A1 | 1/2016 |
| EP | 2967906 A1 | 1/2016 |
| EP | 2719360 B1 | 5/2016 |
| EP | 3016617 A2 | 5/2016 |
| EP | 3031424 A1 | 6/2016 |
| EP | 2729092 B1 | 9/2016 |

(56) References Cited

FOREIGN PATENT DOCUMENTS

| | | | |
|---|---|---|---|
| EP | 2508150 | B1 | 10/2016 |
| EP | 2931181 | B1 | 10/2016 |
| EP | 3076903 | A1 | 10/2016 |
| EP | 3169279 | A1 | 5/2017 |
| EP | 3213720 | A1 | 9/2017 |
| EP | 2967917 | B1 | 11/2017 |
| EP | 3247315 | A1 | 11/2017 |
| EP | 3263072 | A1 | 1/2018 |
| EP | 2654627 | B1 | 3/2018 |
| EP | 3294223 | A1 | 3/2018 |
| EP | 3315095 | A1 | 5/2018 |
| EP | 3344194 | A1 | 7/2018 |
| EP | 3345575 | A1 | 7/2018 |
| EP | 2793760 | B1 | 8/2018 |
| EP | 3362000 | A1 | 8/2018 |
| EP | 3366263 | A1 | 8/2018 |
| EP | 2904991 | B1 | 10/2018 |
| EP | 3397212 | A1 | 11/2018 |
| EP | 2051660 | B1 | 2/2019 |
| EP | 2735286 | B1 | 3/2019 |
| EP | 2747714 | B1 | 4/2019 |
| EP | 3474782 | A2 | 5/2019 |
| EP | 3474783 | A2 | 5/2019 |
| EP | 3474784 | A2 | 5/2019 |
| EP | 2961352 | B1 | 6/2019 |
| EP | 2611395 | B1 | 7/2019 |
| EP | 3240506 | B1 | 7/2019 |
| EP | 3247295 | B1 | 8/2019 |
| EP | 3253335 | B1 | 8/2019 |
| EP | 2958525 | B1 | 9/2019 |
| EP | 3534811 | A1 | 9/2019 |
| EP | 2838454 | B1 | 10/2019 |
| EP | 3177233 | B1 | 10/2019 |
| EP | 2764851 | B1 | 11/2019 |
| EP | 3324895 | B1 | 11/2019 |
| EP | 3568109 | A1 | 11/2019 |
| EP | 3621554 | A1 | 3/2020 |
| EP | 3622920 | A1 | 3/2020 |
| EP | 3638157 | A1 | 4/2020 |
| EP | 2967901 | B1 | 5/2020 |
| EP | 3435924 | B1 | 5/2020 |
| EP | 3310304 | B1 | 9/2020 |
| EP | 3384877 | B1 | 10/2020 |
| EP | 3727207 | A1 | 10/2020 |
| EP | 3742990 | A1 | 12/2020 |
| EP | 3818965 | A1 | 5/2021 |
| ES | 2361099 | B1 | 5/2012 |
| FR | 2763836 | B1 | 7/1999 |
| FR | 2866228 | B1 | 9/2006 |
| FR | 2981261 | B1 | 11/2013 |
| FR | 3058043 | B1 | 11/2020 |
| WO | WO-2006134262 | A1 * | 12/2006 ............. A61F 2/447 |
| WO | WO2014144696 | A1 | 9/2014 |
| WO | WO2016127139 | A1 | 8/2016 |
| WO | WO2019023251 | A1 | 1/2019 |
| WO | WO2019079090 | A1 | 4/2019 |
| WO | WO2019161393 | A1 | 8/2019 |
| WO | WO2019165152 | A1 | 8/2019 |
| WO | WO2019165157 | A1 | 8/2019 |
| WO | WO2019169036 | A1 | 9/2019 |
| WO | WO2019170739 | A1 | 9/2019 |
| WO | WO2019170744 | A1 | 9/2019 |
| WO | WO2019191745 | A1 | 10/2019 |
| WO | WO2019246441 | A1 | 12/2019 |
| WO | WO2020084158 | A1 | 4/2020 |
| WO | WO2020095745 | A1 | 5/2020 |
| WO | WO2020104788 | A1 | 5/2020 |
| WO | WO2020104790 | A1 | 5/2020 |
| WO | WO2020104792 | A1 | 5/2020 |
| WO | WO2020209722 | A1 | 10/2020 |
| WO | WO2020251943 | A1 | 12/2020 |

OTHER PUBLICATIONS

US 11,026,806 B2, 06/2021, Olmos et al. (withdrawn)
Extended European Search Report for corresponding EP Application No. 21186249.5 dated Jan. 17, 2022 (7 pages).
Extended European Search Report for corresponding EP Application No. 21186250.3 dated Jan. 31, 2022 (13 pages).
Extended European Search Report for corresponding EP Application No. 21186251.1 dated Jan. 28, 2022 (11 pages).
Extended European Search Report for corresponding EP Application No. 21186272.7 dated Mar. 2, 2022 (9 pages).
International Search Report and Written Opinion for corresponding PCT Application No. PCT/EP2022/069885 mailed Oct. 19, 2022 (9 pages).
International Search Report and Written Opinion for corresponding PCT Application No. PCT/EP2022/069886 mailed Nov. 3, 2022 (13 pages).
International Search Report and Written Opinion for corresponding PCT Application No. PCT/EP2022069888 mailed Nov. 8, 2022 (13 pages).
International Search Report and Written Opinion for corresponding PCT Application No. PCT/EP2022069906 mailed Nov. 7, 2022 (13 pages).

* cited by examiner

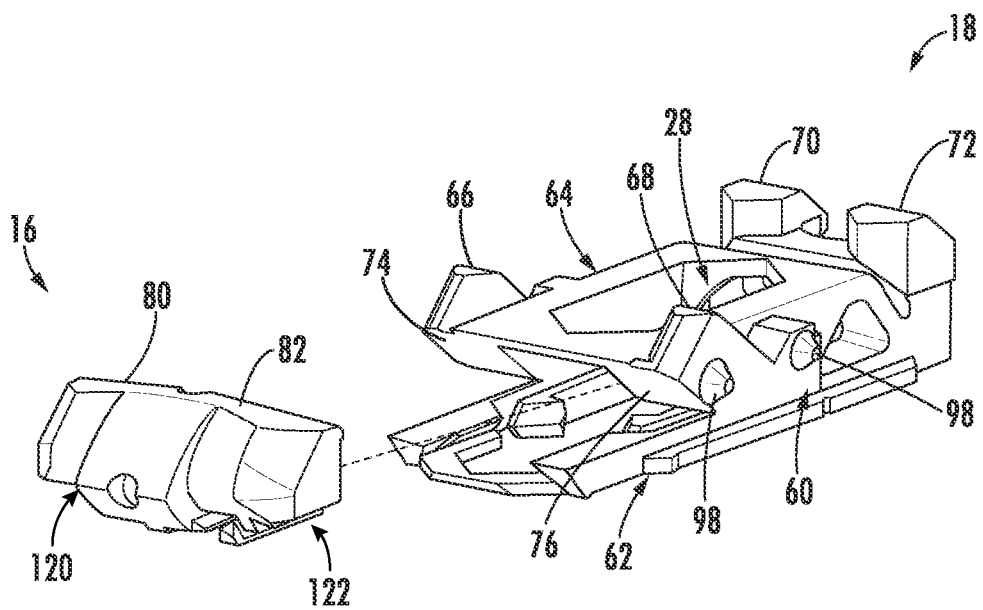
FIG. 5
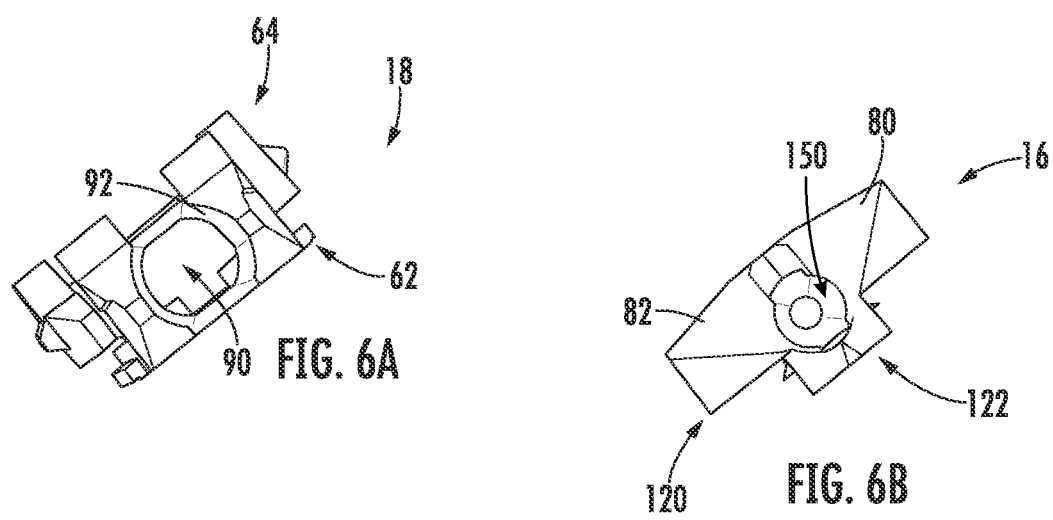
FIG. 6A
FIG. 6B

ADJUSTABLE SPINAL IMPLANTS, ASSOCIATED INSTRUMENTS AND METHODS

CROSS-REFERENCE TO RELATED APPLICATIONS

This application claims the benefit of U.S. Provisional Application Ser. Nos. 63/222,482, 63/222,498 and 63/222,506, all of which were filed Jul. 16, 2021, and European Patent Application Nos. 21186249.5, 21186250.3 21186251.1 and 21186272.7, all of which were filed Jul. 16, 2021, the complete disclosures of which are incorporated herein by reference in their entirety for all purposes.

FIELD

The present disclosure relates to implantable devices for stabilizing and/or promoting the fusion of adjacent bony structures and, more particularly, to implantable spinal fusion cages that can adjust in height and angle to accommodate spacing constraints and/or address lordosis within an intervertebral space.

BACKGROUND

Implantable spinal devices can be used to treat a variety of spinal disorders, including degenerative disc disease. For example, in one type of spinal disorder, the intervertebral disc has deteriorated or become damaged due to acute injury or trauma, disc disease or simply the natural aging process. The standard treatment today may involve surgical removal of a portion, or all, of the diseased or damaged intervertebral disc in a process known as a partial or total discectomy, respectively. The discectomy is often followed by the insertion of an interbody cage or spacer to stabilize this weakened or damaged spinal region and/or to restore disc height. This cage or spacer serves to reduce or inhibit mobility in the treated area, in order to avoid further progression of the damage and/or to reduce or alleviate pain caused by the damage or injury. Moreover, these types of cages or spacers serve as mechanical or structural scaffolds to restore and maintain normal disc height, and in some cases, can also provide a space for inserting bone graft material to promote bony fusion between the adjacent vertebrae.

One of the current challenges of these types of procedures is the very limited working space afforded the surgeon to manipulate and insert the cage into the intervertebral area to be treated. Access to the intervertebral space requires navigation around retracted adjacent vessels and tissues such as the aorta, vena cava, dura and nerve roots, leaving a very narrow pathway for access. The opening to the intradiscal space itself is also relatively small. Hence, there are physical limitations on the actual size of the cage that can be inserted without significantly disrupting the surrounding tissue or the vertebral bodies themselves.

Further complicating the issue is the fact that the vertebral bodies are not positioned parallel to one another in a normal spine. There is a natural curvature to the spine due to the angular relationship of the vertebral bodies relative to one another. The ideal interbody fusion cage must be able to accommodate this angular relationship of the vertebral bodies, or else the cage will not sit properly when inside the intervertebral space. An improperly fitted cage would either become dislodged or migrate out of position, and lose effectiveness over time, or worse, further damage the already weakened area.

Another challenge with implanting interbody fusion cages is that, in order to insert the cage between the adjacent vertebra, at least a portion, if not all, of the intervertebral disc is removed to make room for the cage. The removal of the entire disc or disc portion disrupts the normal lordotic or kyphotic curvature of the spine. Traditional fusion cages do not attempt to correct this curvature, and over time as the vertebrae settle around the implanted cages, kyphotic deformity results.

It is therefore desirable to provide implantable spinal devices that have the ability to maintain and restore the normal anatomy of the fused spine segment. It is particularly desirable to provide interbody cages or spacers that not only have the mechanical strength or structural integrity to restore disc height or vertebral alignment to the spinal segment to be treated, but also can easily pass through the narrow access pathway into the intervertebral space, and accommodate the angular constraints of this space and/or correct the lordotic or kyphotic curvature created by removal of the disc.

SUMMARY

The present disclosure provides adjustable spinal devices and instruments for implanting the spinal devices. The present disclosure further provides methods for adjusting the height and/or lordosis angles of the spinal devices and methods for implanting such devices.

In one aspect, an adjustable spinal fusion device includes an upper plate component having an outer surface for placement against a first vertebral body and a lower plate component having an outer surface for placement against a second vertebral body. The device further includes a translation member configured to move longitudinally relative to the upper and lower plates to adjust an angle between the upper and lower plates (e.g., the angle of lordosis of the implant). Thus, the device has a first configuration for advancing through a narrow access pathway into the intervertebral space, and a second configuration, wherein the device may be adjusted in angle to accommodate the angular constraints of this space and/or correct the lordotic or kyphotic curvature.

In embodiments, the upper and lower endplates each have proximal and distal ends. The proximal ends are pivotally coupled to each other and the distal ends are movable relative to each other to adjust a distance therebetween. The translation member may comprise an angled surface extending downward from the upper endplate towards the lower endplate in the proximal direction. The device may further comprise a ramp for cooperating with the angled surface of the translation member. The device may comprise a hinge pivotally coupling the internal support member to the lower endplate. In certain embodiments, proximal translation of the translation member causes the angled surface to engage the ramp and move the distal end of the upper endplate away from the distal end of the lower endplate such that the proximal ends of the endplates remain substantially fixed relative to each other as the distal ends are moved apart.

In one embodiment, the upper endplate comprises the ramp. In another embodiment, the device further comprises an internal support member coupled to, or integral with, the upper endplate and pivotally coupled to the lower endplate. The lower internal support member comprises the ramp.

In certain embodiments, longitudinal translation of the translation member also adjusts a height of the endplates. In one such embodiment, the upper endplate comprises proximal and distal ramps and the translation member comprises proximal and distal angled surfaces for cooperating with the proximal and distal ramps of the upper endplate to adjust a distance between the proximal and distal ends of the endplates. Thus, longitudinal movement of the translation member relative to the endplates results in adjustment of both the angle and height of endplates.

In certain embodiments, the device may comprise a second translation member. Longitudinal movement of the second translation member relative to the first translation member adjusts the angle between the upper and lower endplates. This allows for independent adjustment of the devices height and angle after it has been implanted between the vertebral bodies. The second translation member may include a second movable wedge with at least one angled surface. The upper and lower endplates may each comprise a ramp for cooperating with the angled surface of the second movable wedge of the second translation member such that longitudinal movement of the second movable wedge adjusts a distance between at least a distal portion of the upper and lower endplates.

In embodiments, the upper and lower endplates are separate components. They may be manufactured separately, or manufactured together and then separated. In embodiments, the translation member, the internal support member and/or the lower endplate comprise at least one projection, such as a pin, extending laterally away from the longitudinal axis. The upper endplate comprises an opening or slot for receiving the projection. The projection(s) are configured to pass through the opening(s) to couple the endplates to each other. In certain embodiments, the projection(s) are located on the translation member and are configured to slide within slot(s) to stabilize the upper and lower endplates during longitudinal movement of the first translation member.

In another embodiment, the device comprises a flexible hinge coupling the upper endplate to the lower endplate. The flexible hinge may comprise a leaf spring having a proximal end coupled to the lower endplate and a distal end coupled to the upper endplate. The hinge may have a relatively small cross-sectional area that creates flexibility in the hinge as the endplates move relative to each other; allowing the hinge to flex with this movement and remain coupled to the endplates. This provides positional stability to the endplates during height and/or angle adjustment.

In embodiments, the device comprises a mechanism for providing discrete "steps" in the movement of the translation member relative to the endplates. These steps correlate with height and/or angle adjustments of the endplates. In one such embodiment, the translation member comprises a plurality of projections and one of the upper or lower endplates comprise a plurality of teeth that cooperate with the projections. The projections move relative to the teeth as the translation member is moved longitudinally. The teeth may comprise spaces therebetween that provide discrete increments of angle and/or height adjustment for the endplates.

In embodiments, the projections and the teeth may also inhibit distal movement of the translation member relative to the endplates. The device may further comprise one or more reset noses coupled to the plurality of projections. The reset noses are movable from a locked position, wherein the teeth inhibit distal movement of the translation member relative to the endplates, to an unlocked position, wherein translation member may be moved distally relative to the endplates.

In another aspect, a spinal fusion system comprises an adjustable spinal fusion device having an upper endplate with an outer surface for placement against a first vertebral body and a lower endplate with an outer surface for placement against a second vertebral body. The device includes a translation member configured to move longitudinally relative to the upper and lower plates to adjust an angle and/or a distance between the upper and lower plates. The system further comprises an instrument having a proximal handle, an elongate shaft and an actuator within the elongate shaft coupled to the proximal handle for moving the translation member longitudinally relative to the upper and lower endplates.

In embodiments, the translation member comprises a bore with a first mating feature and the distal end of the actuator comprises a second mating feature. The first and second mating features cooperating with each other such that longitudinal movement of the actuator shaft causes distal ends of the endplates to move relative to each other to adjust a distance therebetween.

In certain embodiments, the system may further comprise a second translation member and a second rotatable actuator shaft coupled the second translation member. The second rotatable actuator may extend through an inner lumen in the first rotatable actuator.

In embodiments, the upper and lower endplates each have proximal and distal ends. The proximal ends are pivotally coupled to each other and the distal ends are movable relative to each other to adjust a distance therebetween. The translation member may comprise an angled surface extending downward from the upper endplate towards the lower endplate in the proximal direction. The device may further comprise a ramp for cooperating with the angled surface of the translation member. The device may comprise a hinge pivotally coupling the internal support member to the lower endplate. In certain embodiments, proximal translation of the translation member causes the angled surface to engage the ramp and move the distal end of the upper endplate away from the distal end of the lower endplate such that the proximal ends of the endplates remain substantially fixed relative to each other as the distal ends are moved apart.

In one embodiment, the upper endplate comprises the ramp. In another embodiment, the device further comprises an internal support member coupled to, or integral with, the upper endplate and pivotally coupled to the lower endplate. The lower internal support member comprises the ramp.

In certain embodiments, longitudinal translation of the translation member also adjusts a height of the endplates. In one such embodiment, the upper endplate comprises proximal and distal ramps and the translation member comprises proximal and distal angled surfaces for cooperating with the proximal and distal ramps of the upper endplate to adjust a distance between the proximal and distal ends of the endplates. Thus, longitudinal movement of the translation member relative to the endplates results in adjustment of both the angle and height of endplates.

In certain embodiments, the device may comprise a second translation member. Longitudinal movement of the second translation member relative to the first translation member adjusts the angle between the upper and lower endplates. This allows for independent adjustment of the devices height and angle after it has been implanted between the vertebral bodies. The second translation member may include a second movable wedge with at least one angled surface. The upper and lower endplates may each comprise a ramp for cooperating with the angled surface of the second movable wedge of the second translation member such that longitudinal movement of the second movable wedge adjusts a distance between at least a distal portion of the upper and lower endplates.

In embodiments, the upper and lower endplates are separate components. They may be manufactured separately, or manufactured together and then separated. In embodiments, the translation member, the internal support member and/or the lower endplate comprise at least one projection, such as a pin, extending laterally away from the longitudinal axis. The upper endplate comprises an opening or slot for receiving the projection. The projection(s) are configured to pass through the opening(s) to couple the endplates to each other. In certain embodiments, the projection(s) are located on the translation member and are configured to slide within slot(s) to stabilize the upper and lower endplates during longitudinal movement of the first translation member.

In another embodiment, the device comprises a flexible hinge coupling the upper endplate to the lower endplate. The flexible hinge may comprise a leaf spring having a proximal end coupled to the lower endplate and a distal end coupled to the upper endplate. The hinge may have a relatively small cross-sectional area that creates flexibility in the hinge as the endplates move relative to each other; allowing the hinge to flex with this movement and remain coupled to the endplates. This provides positional stability to the endplates during height and/or angle adjustment.

In embodiments, the device comprises a mechanism for providing discrete "steps" in the movement of the translation member relative to the endplates. These steps correlate with height and/or angle adjustments of the endplates. In one such embodiment, the translation member comprises a plurality of projections and one of the upper or lower endplates comprise a plurality of teeth that cooperate with the projections. The projections move relative to the teeth as the translation member is moved longitudinally. The teeth may comprise spaces therebetween that provide discrete increments of angle and/or height adjustment for the endplates.

In embodiments, the projections and the teeth may also inhibit distal movement of the translation member relative to the endplates. The device may further comprise one or more reset noses coupled to the plurality of projections. The reset noses are movable from a locked position, wherein the teeth inhibit distal movement of the translation member relative to the endplates, to an unlocked position, wherein translation member may be moved distally relative to the endplates.

In another aspect, an adjustable spinal fusion device includes an upper plate component having an outer surface for placement against a first vertebral body and a lower plate component having an outer surface for placement against a second vertebral body. The device further includes a translation member configured to move longitudinally relative to the upper and lower plates to adjust a height and/or angle between the upper and lower plates. curvature. One of the translation member or the lower endplate comprises one or more projections extending laterally therefrom that extend through the openings to couple the upper endplate to the lower endplate.

In embodiments, the device is fabricated through additive manufacturing techniques, such as 3D printing. The implant may be formed layer by layer in the longitudinal direction from the proximal end to the distal end. Upon completion of manufacturing, the upper and lower endplates are separated from each other and remain together during use by the projections that extend through the openings of the upper endplate.

In one such embodiment, the device further comprises a support member pivotally coupled to the lower endplate and the one or more projections extend laterally outward form the support member. In another embodiment, the openings are slots and the translation member comprises one or more projections extending laterally therefrom and through the slots to couple the translation member to the upper endplate. In yet another embodiment, the device further comprising a flexible hinge coupling the upper endplate to the lower endplate. The flexible hinge may comprise a leaf spring having a proximal end coupled to the lower endplate and a distal end coupled to the upper endplate.

In embodiments, at least one of the upper and lower endplates comprises a surface with one or more exhaust openings for extracting metal powder from within the device. This allows more efficient extraction of metal powder that may, for example, remain in the cage after 3D printing.

It is to be understood that both the foregoing general description and the following detailed description are exemplary and explanatory only and are not restrictive of the disclosure. Additional features of the disclosure will be set forth in part in the description which follows or may be learned by practice of the disclosure.

BRIEF DESCRIPTION OF THE DRAWINGS

The accompanying drawings, which are incorporated in and constitute a part of this specification, illustrate several embodiments of the disclosure and together with the description, serve to explain the principles of the disclosure.

FIG. 5 is a perspective view of proximal and distal translation members of the spinal device;

FIG. 6A is a proximal view of the proximal translation member;

FIG. 6B is a proximal view of the distal translation member;

DESCRIPTION OF THE EMBODIMENTS

Figure 1:
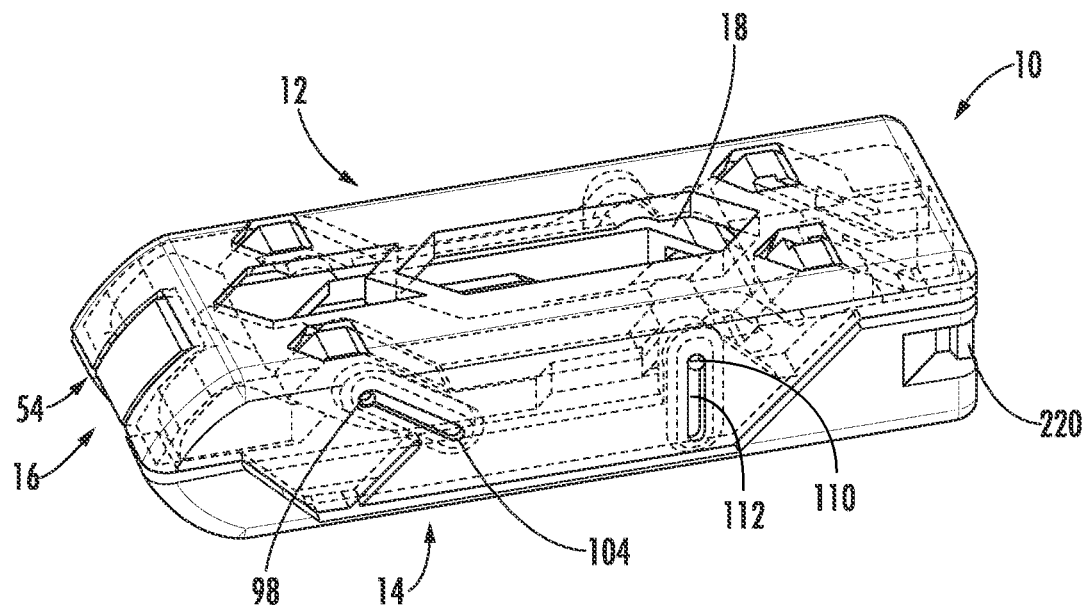
FIG. 1 is a partially transparent view of an implantable spinal device.
Figure 2:
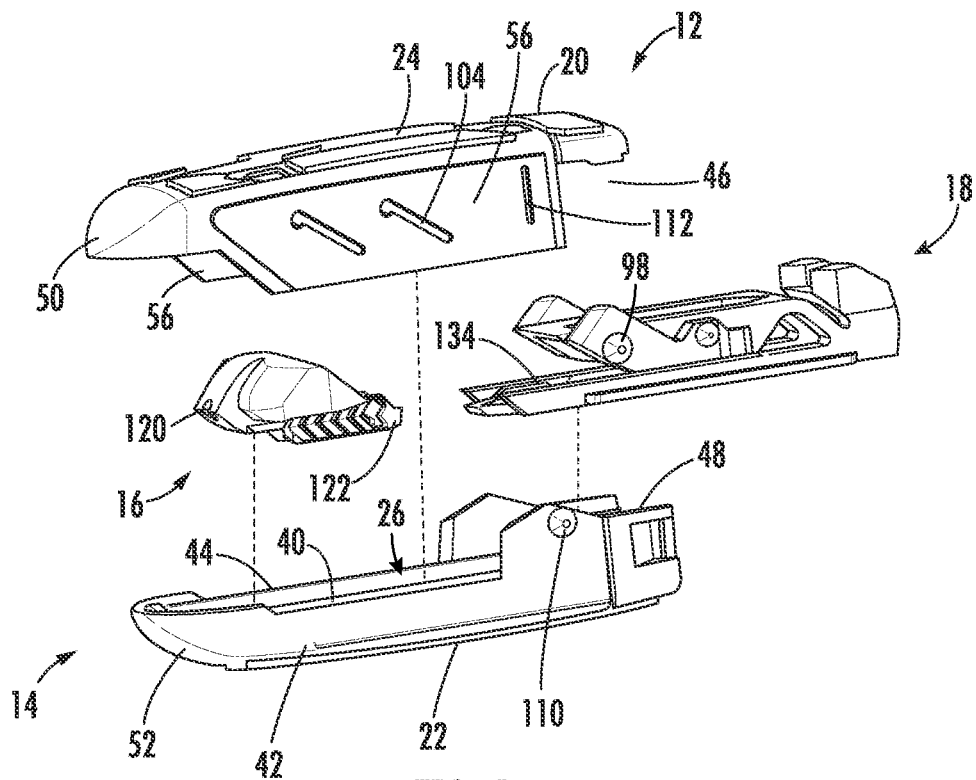
FIG. 2 is an exploded view of the spinal device of FIG. 1.

This description and the accompanying drawings illustrate exemplary embodiments and should not be taken as limiting, with the claims defining the scope of the present disclosure, including equivalents. Various mechanical, compositional, structural, and operational changes may be made without departing from the scope of this description and the claims, including equivalents. In some instances, well-known structures and techniques have not been shown or described in detail so as not to obscure the disclosure. Like numbers in two or more figures represent the same or similar elements. Furthermore, elements and their associated aspects that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment. Moreover, the depictions herein are for illustrative purposes only and do not necessarily reflect the actual shape, size, or dimensions of the system or illustrated components.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

Referring now to FIGS. 1-14, one embodiment of a spinal implant 10 according to the present disclosure is configured for placement between two vertebral bodies. In some embodiments, implant 10 is particularly useful for placement from a posterior approach outside of the facet joint (transforaminal lumbar interbody fusion or TLIF), although it will be recognized that the implants disclosed herein may be employed in a variety of different surgical approaches, such as anterior lumbar interbody fusion (ALIF), posterior lumbar interbody fusion (PLIF) and/or lateral lumbar interbody fusion (LLIF). Spinal implant 10 includes upper and lower endplates 12, 14, a distal translation member 16 and a proximal translation member 18. Movement of translation members 16, 18 in the longitudinal direction relative to endplates 12, 14 changes the height and angle of endplates 12, 14, as discussed in more detail below.

The spinal implant shown in FIGS. 1-14 has at least three different embodiments: (1) the base design; (2) the spring embodiment; and (3) the slot embodiment. The following description is common to all three embodiments. The additional features of the spring and slot embodiments will be described below.

Upper and lower endplates 12, 14 each include an outer surface 20, 22 for contacting the surface of a vertebral body. Outer surfaces 20, 22 are preferably roughened with a surface treatment that facilitates attachment to the vertebral body. The surface treatment preferably creates a diamond structure (e.g., diamond 20-1.5), although other patterns may be used. Upper and lower endplates also include central openings 24, 26 that extend through the entire endplates and, in one embodiment, are substantially aligned with each other. Similarly, proximal translation member 18 includes a central opening or bore 28 that, in one embodiment, may be substantially aligned with endplate openings 24, 26. These openings create space for the addition of bone graft or other substances into the implant, as well as to allow for bony ingrowth through the implant 10.

Figure 4:
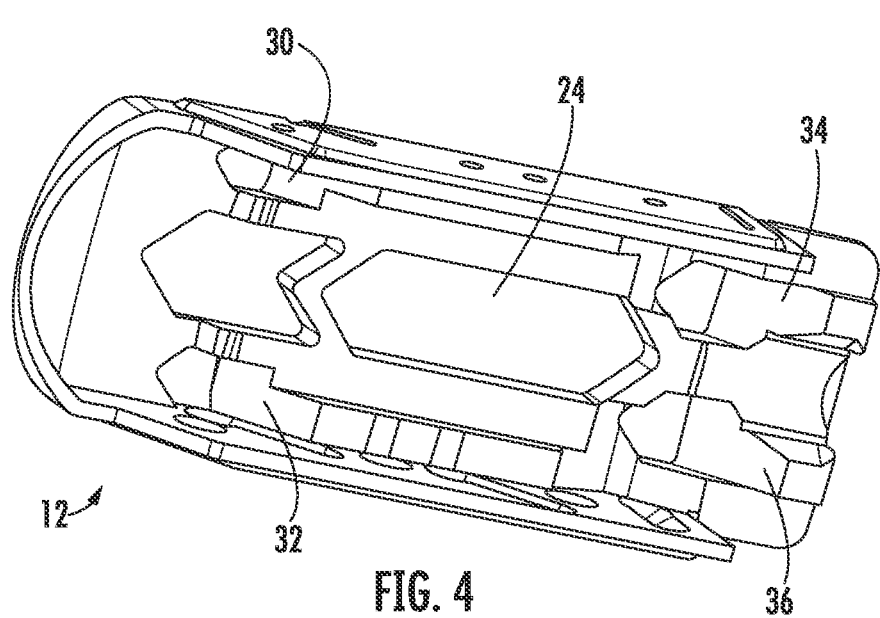
FIG. 4 is a bottom view of the upper endplate.

As shown in FIG. 4, upper endplate 12 includes: (1) first and second distal sloped surfaces or ramps 30, 32 that are laterally spaced from each other near either side of the upper endplate and extend towards lower plate 14 in the proximal direction; and (2) third and fourth proximal sloped surfaces or ramps 34, 36 that are laterally spaced from each other near either side of the endplate and also extend towards lower endplate 14 in the proximal direction. These ramps interact with wedges on proximal translation member 18 to provide height adjustment of the implant (discussed below). In an alternative embodiment, upper endplate 12 may include a single distal ramp and/or a single proximal ramp that extends laterally across a central portion of the endplate 12. Alternatively, endplate 12 may include more than two distal or proximal ramps.

Lower endplate 14 includes a central channel 40 for receiving a lower portion 62 of proximal translation member 18 therein, and for allowing longitudinal movement of proximal translation member 18 relative to the endplates 12, 14. Central channel 40 is bound by first and second internal side walls 42, 44 that extend in a longitudinal direction from a proximal end to a distal end of the endplate.

Figure 14:
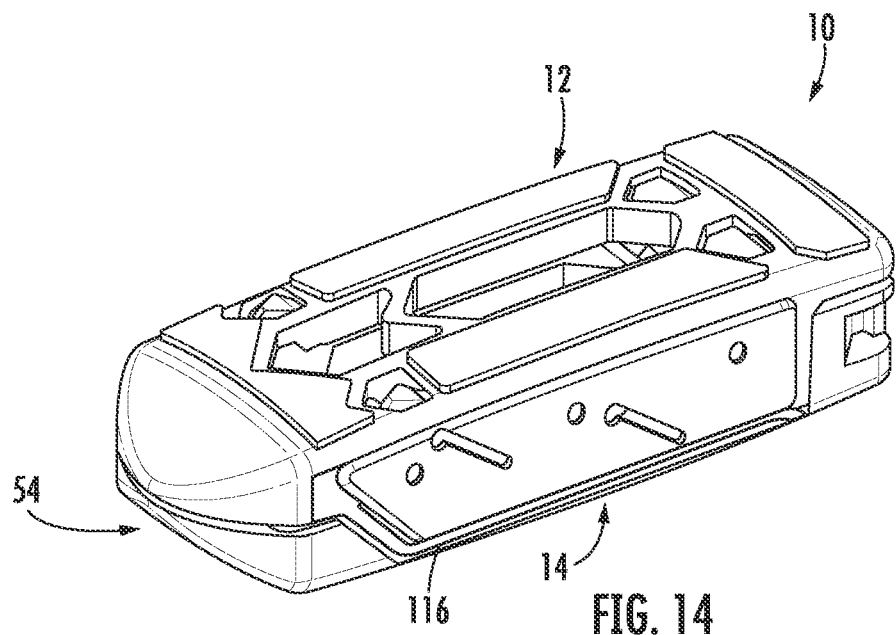
FIG. 14 is side view of another embodiment of a spinal device.

Upper and lower endplates 12. 14 have substantially open proximal ends 46, 48 and tapered distal ends 50, 52 to form a closed wedge-shaped nose 54 at the distal end of the implant (see FIG. 14). Upper endplate 12 includes two side walls 56 that extend downward towards, and at least partially overlap with, side walls 42, 44 of lower endplate 14.

As shown in FIG. 5, proximal translation member 18 includes a main body 60 that extends through a portion of the implant between the endplates. Main body 60 includes a lower portion 62 positioned within channel 40 of lower endplate 14 and configured to translate through this channel relative to endplates 12, 14. Main body 60 further includes an upper portion 64 that is coupled to, or integral with, lower portion 62 at the distal end of translation member 18. Upper and lower portions 64, 62 both include a central opening 28 substantially aligned with the central openings 24, 26 of the endplates for receiving graft material and for allowing bony ingrowth.

Upper portion 64 of proximal translation member 18 includes first and second distal sloped surfaces or wedges 66, 68 that are configured to contact and engage first and second distal ramps 30, 32 of the upper endplate 12, and first and second proximal surfaces or wedges 70, 72 that are configured to contact and engage first and second proximal ramps 34, 36 of the upper endplate 12. Longitudinal movement of proximal translation member 18 causes these wedges to move along the ramps of the upper endplate, thereby moving the upper endplate towards or away from the lower endplate.

Upper and lower portions 62, 64 of the proximal translation member are separated from each other at their proximal ends to receive distal translation member 16. Thus, a portion of the distal translation member extends into the proximal translation member. Upper portion 64 of proximal translation member 18 further includes first and second sloped surfaces or ramps 74, 76 that are laterally spaced from each other and extend downwards towards lower endplate 14 in the proximal direction. These ramps 74, 76 are configured to engage with wedges 80, 82 on distal translation member 16 to adjust the angle of the implant, as discussed below.

As shown in FIG. 6A, proximal translation member 18 further includes a central bore 90 through at least its proximal end for receiving a first rod 202 of an insertion instrument 200 (discussed below; see FIG. 16). Bore 90 includes an annular mating feature configured to receive, and couple to, a mating feature of the rod 202 (see FIG. 17A). In an exemplary embodiment, this mating feature includes a cavity or cut-out 92 sized to receive an enlarged distal end 206 of rod 202. Cavity 92 includes a proximal rim or projection (not shown) that extends towards the longitudinal axis and has a smaller inner diameter than the inner diameter of cavity 92 and the outer diameter of enlarged distal end 206. Enlarged distal end 206 of first rod 202 is tapered on its distal surface. The rim or projection is sufficiently flexible to allow the tapered surface of enlarged distal end 206 to push past the rim (by bending it) and become secured within cavity 92. The rim is sufficiently rigid to inhibit enlarged end 206 of rod 202 from pushing past it in the proximal direction when the rod is pulled in the proximal direction. Once the insertion instrument rod 202 is coupled to proximal translation member 18, longitudinal translation of rod 202 causes proximal translation member 18 to move longitudinally relative to the endplates 12, 14, thereby moving the endplates towards or away from each other.

Figure 10:
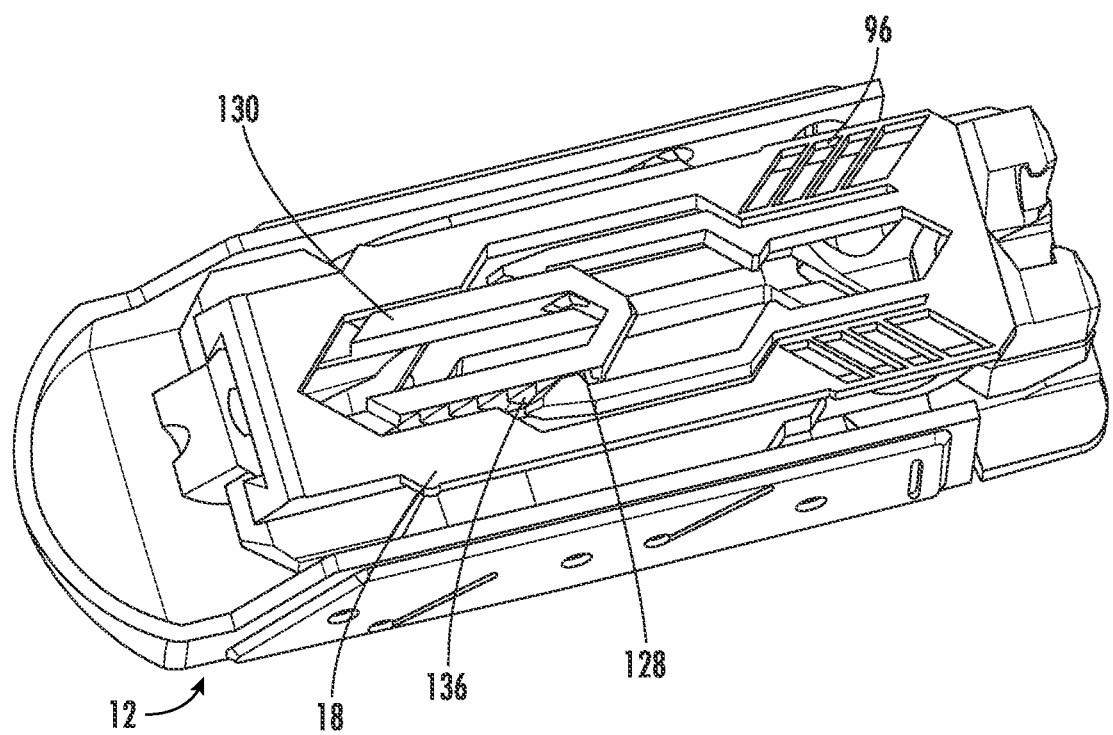
FIG. 10 is a partially cut-a-way view of the clicker system.

As shown in FIGS. 9A, 9B and 10, lower endplate 14 further includes a "clicker arm" 100 for providing discrete "steps" in the movement of proximal translation member 18 relative to the endplates. These steps correlate with height adjustments of the endplates. To this end, proximal translation member 18 comprises a series of projections or teeth 96 extending from its lower surface towards lower endplate 14. Clicker arm 100 includes a plurality of projections (not shown) extending upwards and configured to extend into the spaces formed between teeth 96 of proximal translation member 18. As proximal translation member 18 moves longitudinally, the projections are configured to move from the space between two teeth 96 to the space between adjoining teeth. These spaces provide the discrete steps or increments. In addition, teeth 96 hold translation member 18 in position relative to endplate 12 to maintain a particular height or distance between the upper and lower endplates. The projections also inhibit reverse movement (i.e., distal movement) of the proximal translation member relative to the endplates.

In an alternative embodiment, upper endplate 14 may include the clicker arm (not shown) and proximal translation member 18 may include projections or teeth (not shown) that extend upwards towards the clicker arm on upper endplate 14. Alternatively, both upper and lower endplates 12, 14 may include clicker arms.

Figure 3:
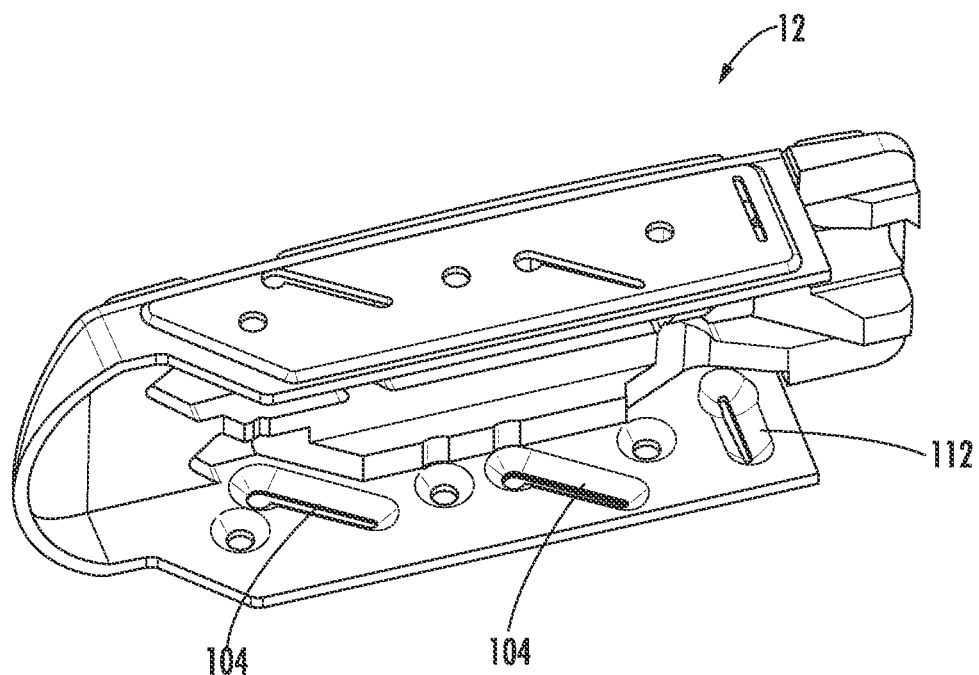
FIG. 3 is a side view of an upper endplate of the spinal device.

Referring to FIGS. 3 and 5, proximal translation member 18 further includes one or more projections, such a pins or the like extending laterally away from translation member 18. In an exemplary embodiment, these projections comprise pins 98 that taper outward to form a substantially conical shape. These conical pins 98 extend through slots 104 in side surfaces 56 of upper endplate 12 and serve to stabilize the endplates during height and angular adjustment (i.e., pins 98 ride through slots 104 as proximal translation member 18 is moved longitudinally related to the endplates 12, 14). In one embodiment translation member 18 includes at least two conical pins 98 on each side spaced longitudinally from each other and configured to ride through angled slots 104 in side surfaces 56 of upper endplate 12.

In the Slot embodiment (see FIGS. 2 and 3), lower endplate 14 also includes a projection, such as a conical-shaped pin, 110 extending laterally outward from each side of the endplate 14. These conical pins 110 are configured to extend through substantially vertical slots 112 in the sides of the upper endplate 12 to provide further positional stabilization (i.e., pins 110 move along slots 112 as endplates 12, 14 move towards and away from each other).

In the Spring embodiment (see FIG. 14), upper and lower endplates further include first and second flexible hinges or leaf springs 116 on either side of the endplates that couple the endplates together to further stabilize the endplates. The endplates are separate components that are only coupled to each other by leaf springs 116 and the connections created by the various conical pins riding through slots in the upper endplate (discussed above). Leaf springs 116 are each formed as an elongate component that extends from a proximal portion of the lower endplate to a distal portion of the lower endplate. The elongate component has a relatively small cross-sectional area that creates flexibility in the elongate component as the endplates move relative to each other; allowing it to flex with this movement and remained coupled to the endplates. This provides positional stability to the endplates during height and angle adjustment.

As shown in FIGS. 1, 5 and 6A, distal translation member 16 comprises a main body 120 positioned near the distal end of the endplates and an extension member 122 extending proximally from main body 120. In certain embodiments, extension member 122 is positioned substantially underneath main body 120 and may not extend proximally therefrom. Main body 120 further includes first and second sloped surfaces or wedges 80, 82 laterally spaced from each other and extending downwards towards the lower endplate 14 in the proximal direction. The wedges 80, 82 are configured to contact and engage ramps 74, 76 on proximal translation member 18 such that movement of distal translation member 16 in the proximal direction relative to proximal translation member 18 causes a distal end portion of proximal translation member 18 to move upwards or away from lower endplate 14. This movement causes the distal end portion of upper endplate 12 to also move away from lower endplate 14, thereby adjusting the angle between the endplates.

Figure 8A:
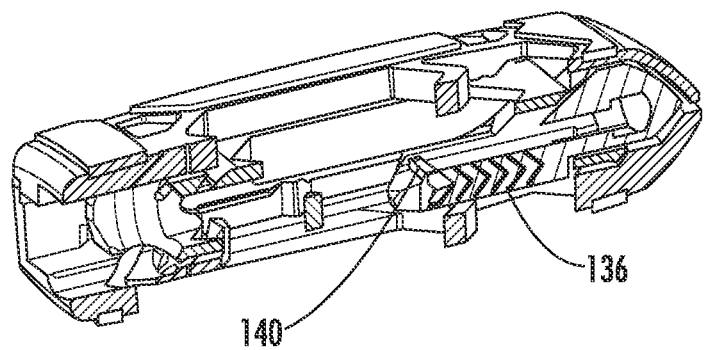
FIG. 8A is an interior view of a portion of the spinal device, illustrating a clicker system for incremental increases in height and angle.
Figure 8B:
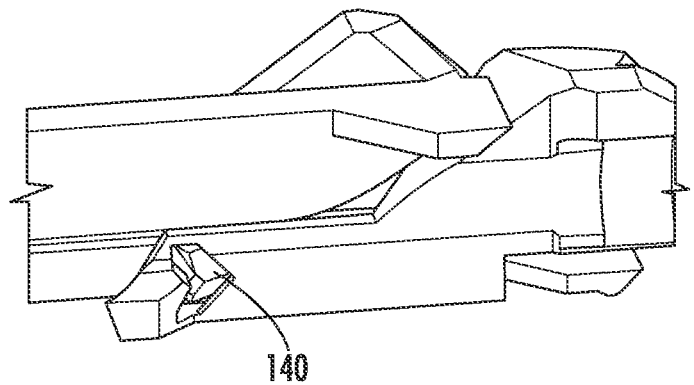
FIG. 8B is a side view of a portion of the first and second translation members, illustrating one feature of the clicker system.
Figure 8C:
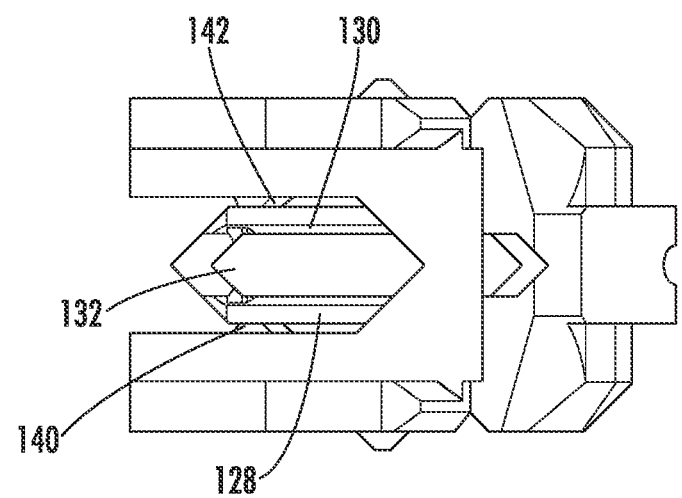
FIG. 8C is a top view of the first and second translation members, illustrating other features of the clicker system.
Figure 9:
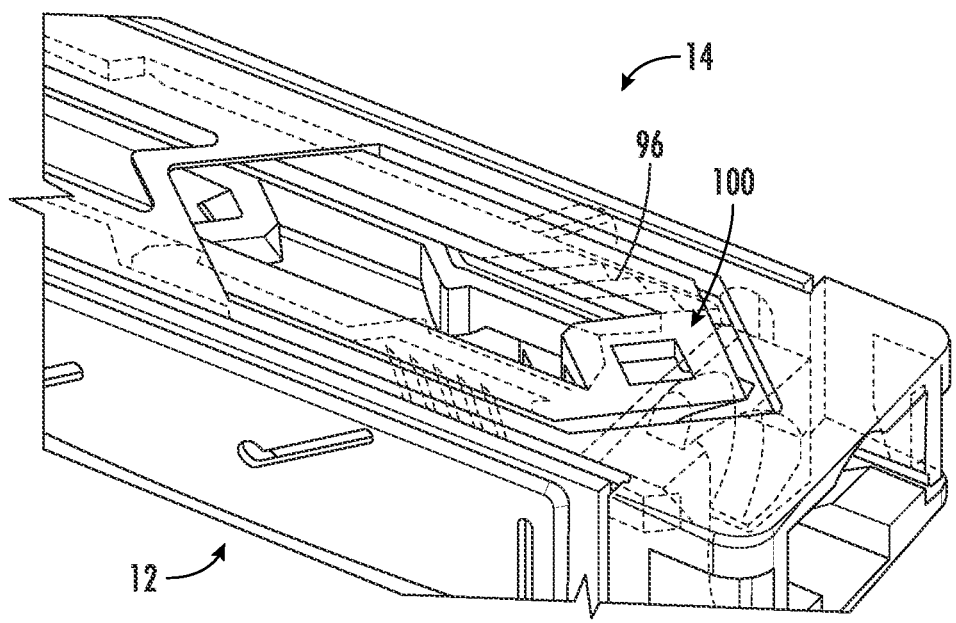
FIG. 9 illustrates the clicker system on the lower endplate of the spinal implant.

As shown in FIG. 8C, extension member 122 of the distal translation member includes two longitudinal supports 128, 130 that form a central channel 132 therebetween. Longitudinal supports 128, 130 are positioned within a channel 134 formed in lower portion 62 of the proximal translation member 18 (see FIG. 2). Longitudinal supports 128, 130 are also configured to translate through this channel 134 during angle adjustment (discussed below).

Each of the longitudinal supports 128, 130 of distal translation member 16 include a series of projections or teeth 136 formed on the outer side of these supports 128, 130 (see FIG. 8A). Teeth 136 are configured to engage two lateral projections 140, 142 extending from the inner surfaces of lower portion 62 of proximal translation member 18 to provide discrete "steps" as distal translation member 16 is moved in relation to proximal translation member 18 (see FIG. 8C). Each "step" corresponds to a specific angle change in the endplates and allows the endplates to be locked into a particular angle. Projections 140, 142 also inhibit reverse movement (i.e., distal movement) of distal translation member 16 relative to proximal translation member 18.

In the slot and spring embodiments, the distal translation member has a different overall shape than in the base embodiment. Extension member 122 is partially located beneath main body 120 and partially extends from main body 120 in the proximal direction.

Figure 17A:
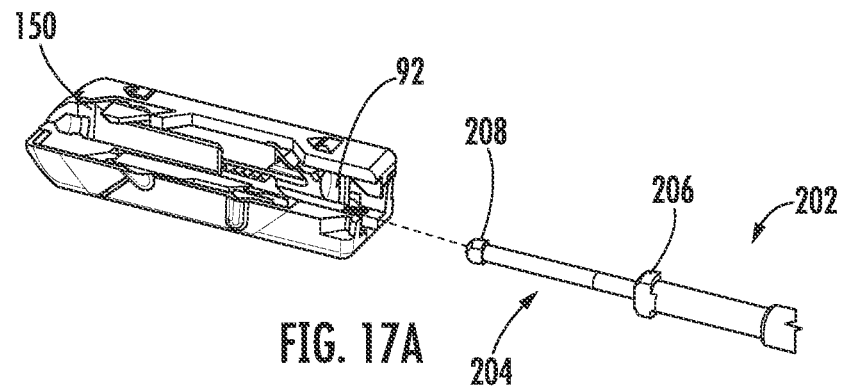
FIGS. 17A and 17B illustrate first and second shaft actuators of the instrument for adjusting height and angle of the spinal device.
Figure 17B:
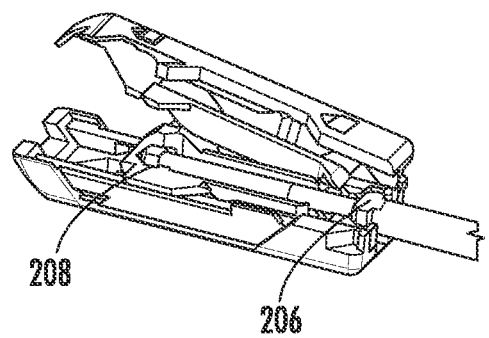
Figure 18:
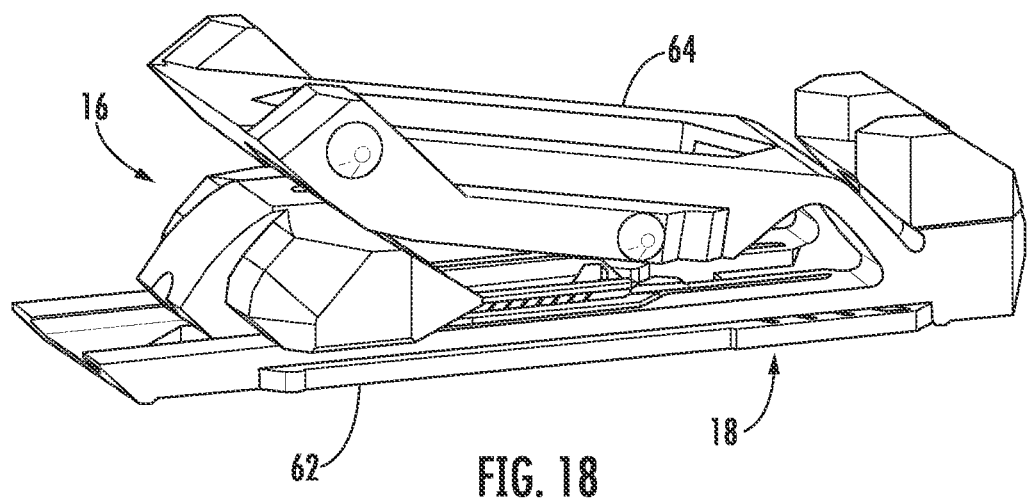
FIG. 18 illustrates the first and second translation members adjusting the angle of the spinal device.

As shown in FIGS. 17A and 17B, distal translation member 16 further includes a mating feature configured to receive, and couple to, an enlarged distal end 208 of a second rod 204 on the insertion instrument (discussed below). The mating feature includes a cavity or cut-out 150 sized to receive enlarged distal end 208 of rod 204. Cavity 150 includes a proximal rim or projection that extends towards the longitudinal axis and has a smaller inner diameter than the inner diameter of cavity 150 and the outer diameter of enlarged distal end 208. Enlarged distal end 208 of rod 204 is tapered on its distal surface. The rim is sufficiently flexible to allow the tapered surface of enlarged distal end 208 to push past the rim (by bending it) and become secured within cavity 150. The rim is sufficient rigid to inhibit enlarged end 208 of rod 204 to push past it in the proximal direction when rod 204 is pulled in the proximal direction. Thus, once rod 204 is coupled to distal translation member 16, longitudinal translation of rod 204 causes distal translation member 16 to move longitudinally relative to proximal translation member 18 and endplates 12, 14, thereby adjusting the angle of the endplates.

Figure 11:
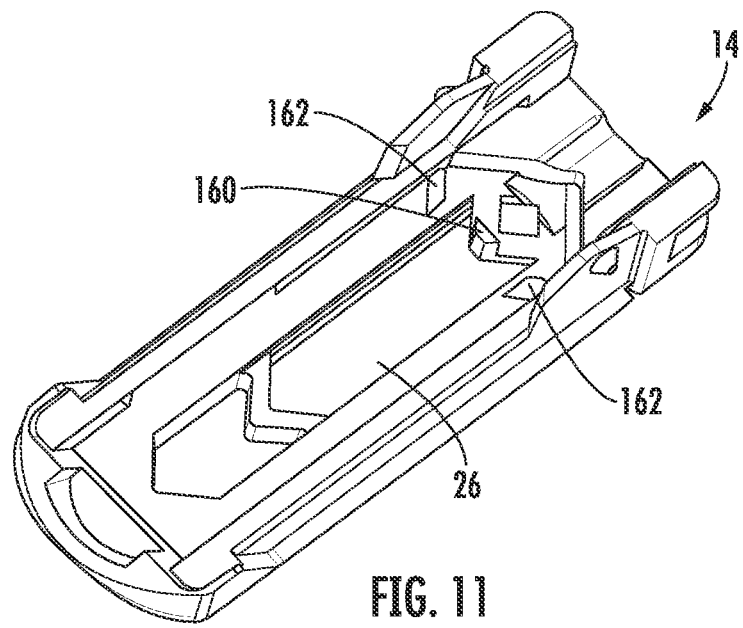
FIG. 11 is a top view of the lower endplate of the spinal device.
Figure 12:
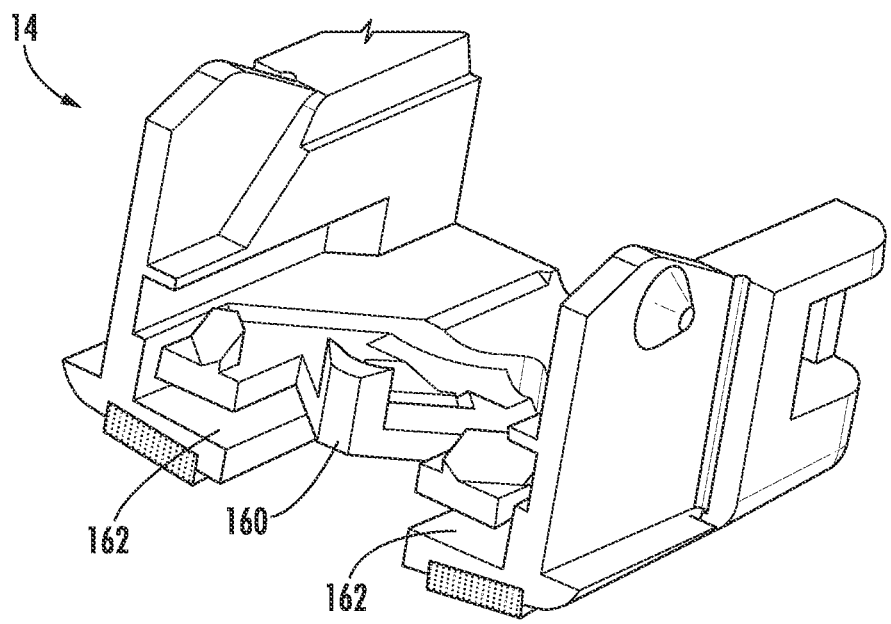
FIG. 12 is a cut-a-way view of a portion of the lower endplate.
Figure 13:
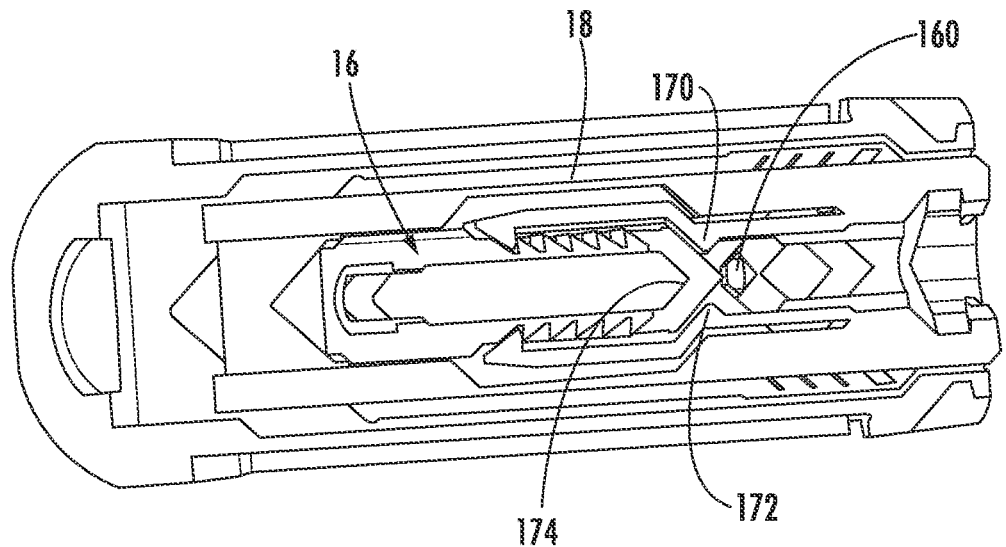
FIG. 13 is another cut-a-way view of a portion of the spinal device.

Referring now to FIGS. 11-13, lower implant 14 can further comprise one or more reset noses 160, 170, 172, which are configured to release the latched latching components in a controlled manner. Thus, the height and the lordosis can be readjusted if they are adjusted above their specific target value. Pushing reset nose 160 results in pushing the latching component, e.g. latching nose 162, apart from the latching position. Thus, the component comprising the latching component can be readjusted. Reset nose 160 can be positioned near and/or attached to the flexible latching component.

As shown in FIG. 13, proximal translation member 18 may include two reset noses 170, 172. If these noses 170, 172 are pushed, distal translation member 16 can be readjusted. Noses 170, 172 can be pushed by rotating locking rod 204 corresponding to distal translation member 16 before it has reached the locking position, e.g., before entering the cage, and then by pushing locking rod 204 into the implant until it has reached reset noses 170, 172.

Lower implant 14 may also include a reset nose 160. If reset nose 160 is pushed, proximal translation member 18 can be readjusted. It can be pushed by pushing the corresponding locking rod 202 into the implant beyond the locking position without rotating it. As shown, reset nose 160 is preferably positioned on lower endplate 14 and not on the upper endplate 12 because upper endplate 12 is lifted from the lower endplate 14. This would result in lifting the corresponding reset nose 160 away from the locking rod 202 which then cannot reach and push the reset nose 160. Preferably, distal translation member comprises a recess 174 to enable the corresponding locking rod 202 to reach the reset position, especially if the distal translation member 16 is pulled to the most far position inside the proximal translation member 18.

Figure 15:
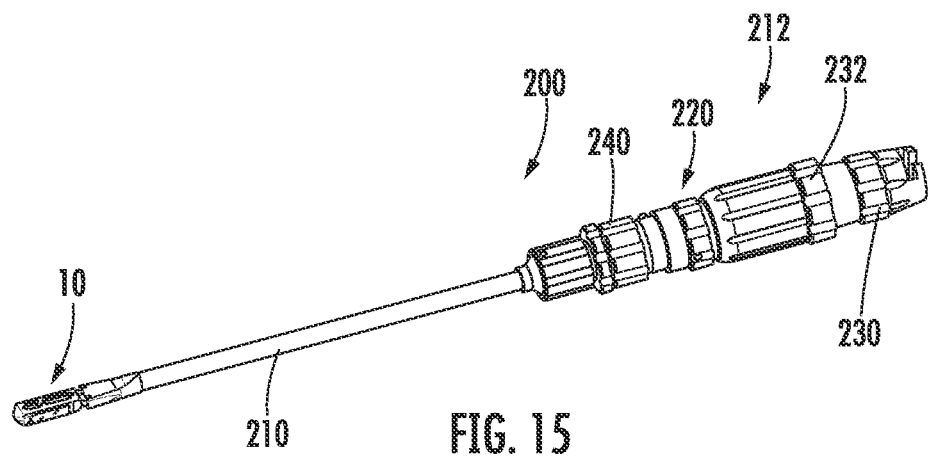
FIG. 15 is a perspective view of an instrument for implanting the spinal devices disclosed herein between adjacent vertebral bodies.
Figure 16:
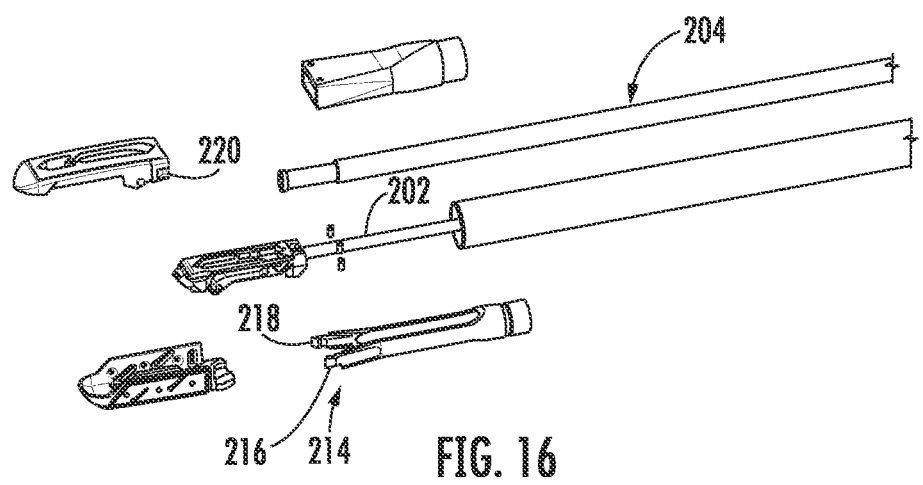
FIG. 16 is an exploded view of the instrument of FIG. 15.

Referring now to FIGS. 15-17, insertion instrument 200 comprises an elongated shaft 210 with a proximal handle 212 and a distal gripping element 214 for removable coupling to spinal implant 10. Distal gripping element 214 includes first and second gripping arms 216, 218 for coupling to proximal mating features 220 on either side of the upper endplate (a bayonet style connection: see also FIG. 1). Distal gripping arms 216, 218 are coupled to an actuator 220 on the proximal handle 212 to move arms 216, 218 in a substantially lateral direction relative to the longitudinal axis of shaft 210. Arms 216, 218 can be moved together to hold lower endplate 14 and moved apart to release lower endplate 14.

Elongate shaft 210 includes inner and outer concentric rods 202, 204. Inner rod 202 can be extended from handle 212 to distal translation member 16 and outer rod 204 can be extended from handle 212 to proximal translation member 18. Inner and outer rods 202, 204 are both attached to rotatable knobs 230, 232 on proximal handle 212 for translating the rods 202, 204 longitudinally relative to shaft 210. Inner rod 202 has an enlarged distal end 206 that may be coupled to cavity 150 of distal translation member 16 and outer rod 204 has an enlarged distal end 208 that can be coupled to cavity 92 on proximal translation member 18.

Handle 212 may further include a third rotatable knob 240 coupled to shaft 210 for rotating shaft 210 and endplates 12, 14 therewith relative to handle 212. This allows for rotation of the endplates without rotating the handle to facilitate ease of use during implantation.

Figure 7A:
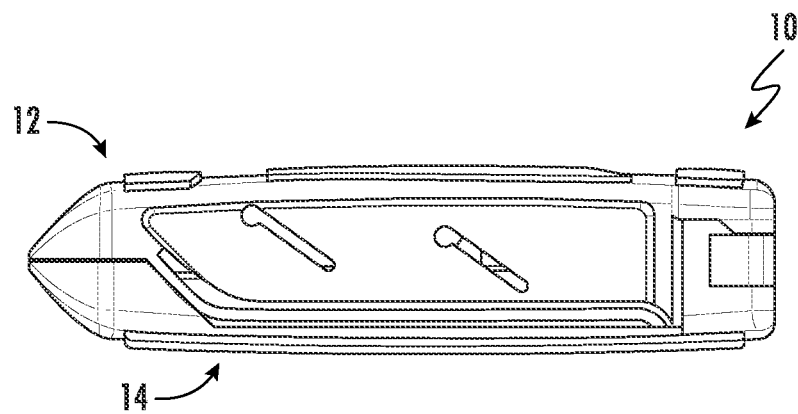
FIG. 7A is a side view of the spinal device in a configuration for insertion between two adjacent vertebral bodies.
Figure 7B:
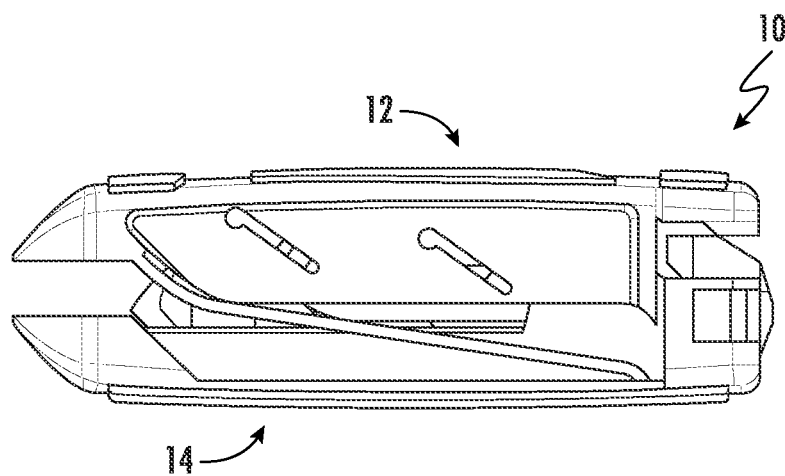
FIG. 7B is a side view of the spinal device with increased height or distance between the upper and lower endplates.
Figure 7C:
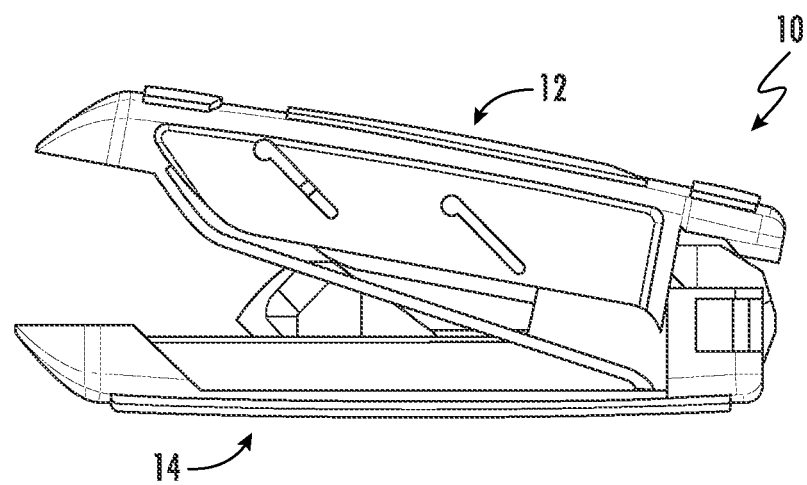
FIG. 7C is a side view of the spinal device with increased distance and lordosis angle between the upper and lower endplates.

In use, implant 10 may be advanced into an intervertebral space in a collapsed configuration (see the resting state shown in FIG. 7A). To increase the height of the implant, endplates 12, 14 are moved away from each other in a substantially parallel direction. To that end, inner and outer rods 202, 204 may be advanced distally and coupled to translation members 16, 18, as discussed above. Rotatable knob 230 on proximal handle 212 may then be rotated to thereby withdraw outer rod 202 proximally. This translates both the proximal and distal translation members 16, 18 in the proximal direction. As distal translation member 18 moves in the proximal direction, its wedges engage with the upper endplate ramps such that endplates 12, 14 move apart from each other in a substantially parallel direction (see expanded state shown in FIG. 7B).

To adjust the angle of endplates 12, 14, rotatable knob 232 on proximal handle 212 may be rotated, causing inner rod 204 to move in the proximal direction. Inner rod 204 pulls distal translation member 16 proximal relative to both endplates 12, 14 and proximal translation member 18. The wedges on distal translation member 16 contact and engage the ramps on proximal translation member 18, causing the distal end portion of proximal translation member 18 to move upwards away from lower endplate 14. This also causes the distal end portion of upper endplate 12 to move away from lower endplate 14. Since proximal translation member 18 does not move, the proximal ends of the endplates remain fixed relative to each other, thereby adjusting the angle of the upper endplate relative to the lower endplate (see angularly adjusted state shown in FIG. 7C).

The process of height and angle adjustment is reversible. The height and angle may also be adjusted independently of each other. For example, the above process can be reversed such that the inner rod is first withdrawn proximally to adjust angle, and then the outer rod is withdrawn proximally to adjust height.

Figure 19:
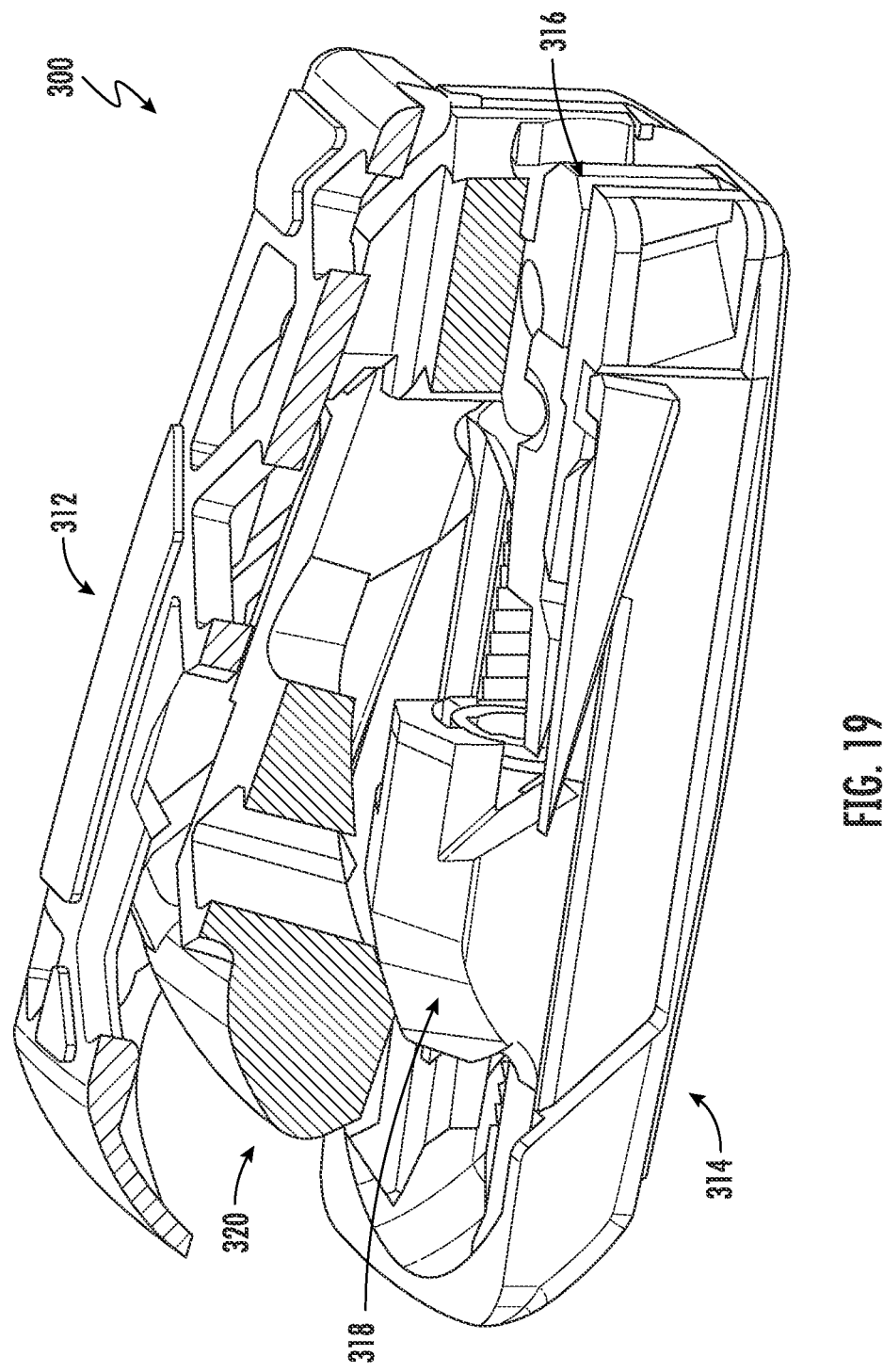
FIG. 19 is a partially cut-a-way view of another embodiment of a spinal device.
Figure 20:
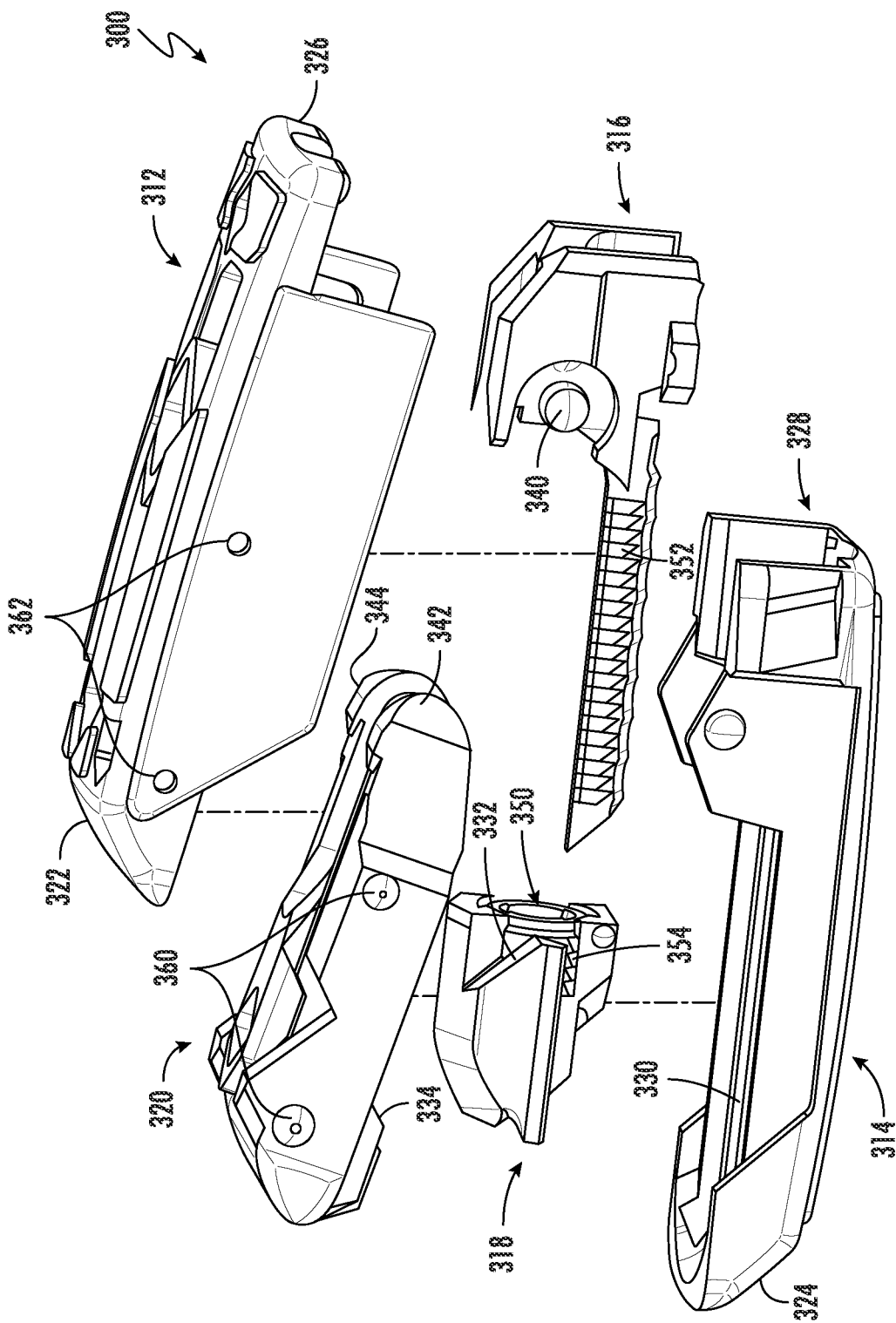
FIG. 20 is an exploded view of the spinal device of FIG. 19.
Figure 21:
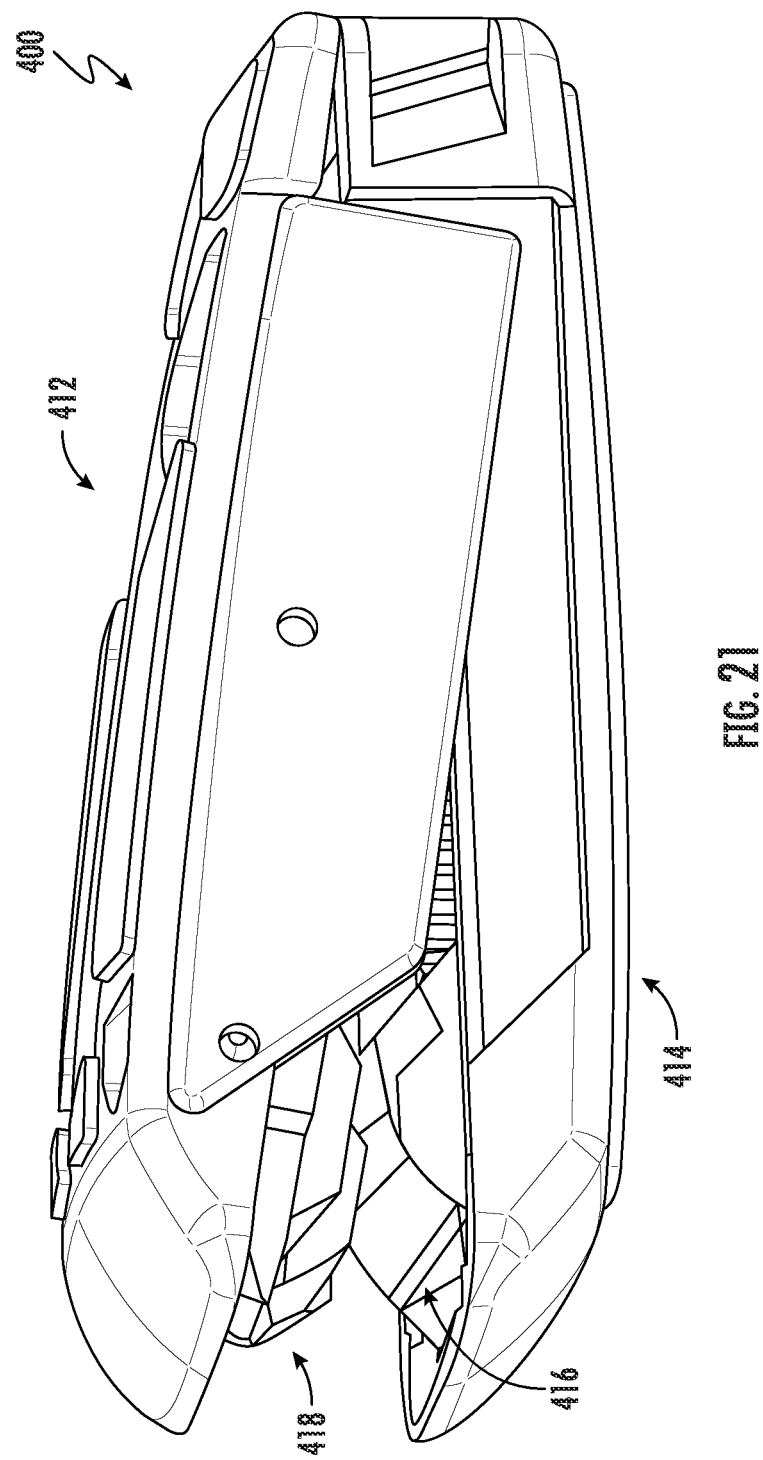
FIG. 21 is a perspective view of another embodiment of a spinal device.
Figure 22:
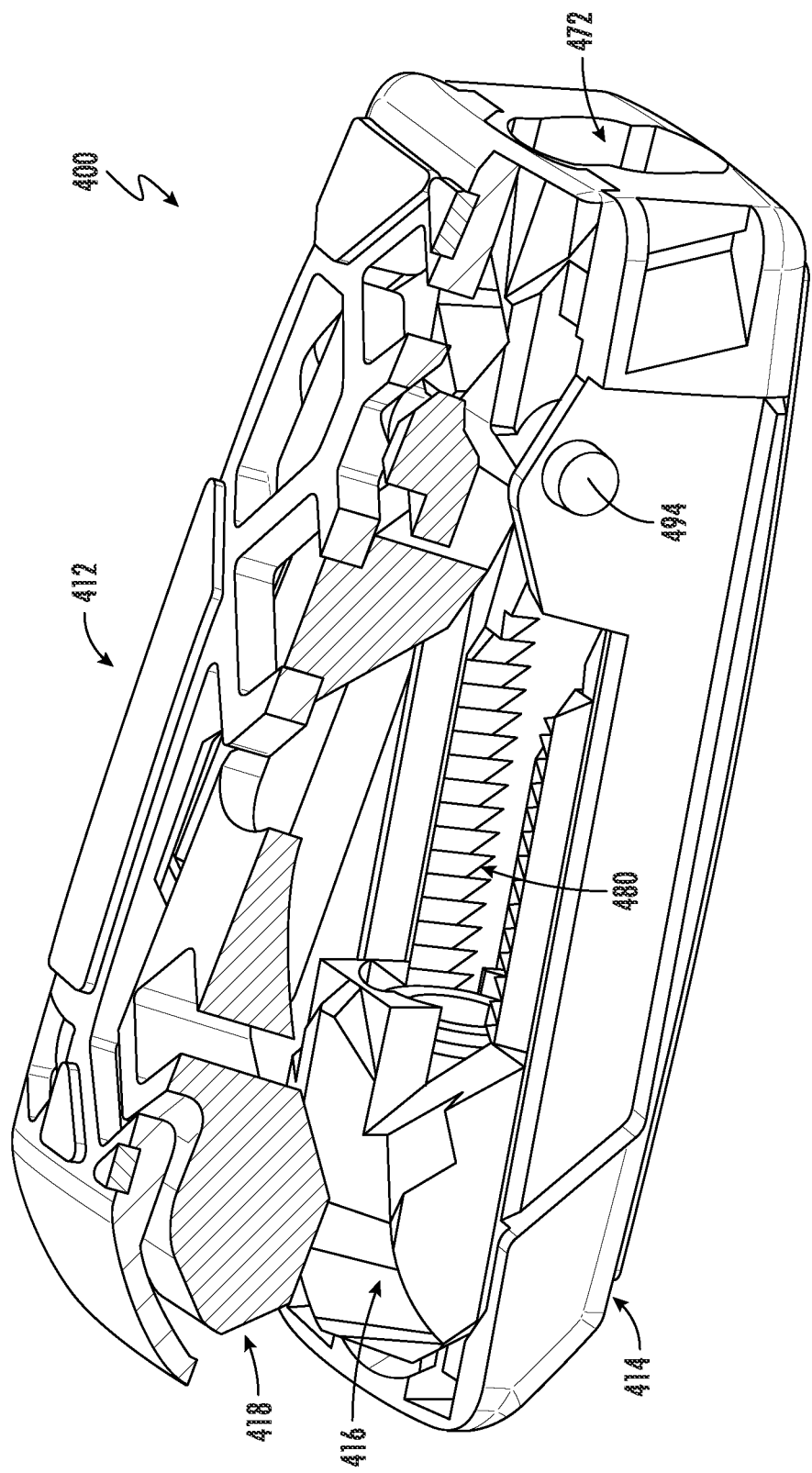
FIG. 22 is a partially cut-a-way view of the spinal device of FIG. 21.

Referring now to FIGS. 19 and 20, another embodiment of a spinal implant 300 will be described. Spinal implant 300 generally has similar features as spinal implant 10 except where described herein. As shown, implant 300 includes upper and lower endplates 312, 314, an internal support member 316 and first and second translation members 318, 320. In this embodiment, the angle between upper and lower endplates 312, 314 may be adjusted. However, the height or distance between the endplates is not adjustable. More specifically, the distance between distal ends 322, 324 of endplates 312, 314 may be adjusted whereas the distance between proximal ends 326, 328 generally remains fixed.

Internal support member 316 may be coupled to, or integral with, lower endplate 314. Second translation member 320 may be coupled to, or integral with, upper endplate 314. Second translation member is pivotally coupled to support member 316 with a hinge located near proximal ends 326, 328 of endplates 312, 314. This hinge allows second translation member 320 and upper endplate 312 to pivot relative to support member 316 and lower endplate 314 around an axis substantially perpendicular to the longitudinal axis of implant 300. In an exemplary embodiment, support member 316 includes projections 340 on either side that are designed to cooperate with openings or channels (not shown) in second translation member 320 to form the hinge. Thus, second translation member 320 includes first and second proximal arms 342, 344 designed to fit on either side of support member 316 such that the projections 340 extend into the openings or channels on arms 342, 344.

Lower endplate 314 includes a central channel 330 for receiving internal support member 316 and first translation member 318. First translation member 318 is movable in the longitudinal direction relative to support member 316, endplates 312, 314 and second translation member 320. Similar to previous embodiments, first translation member 316 includes one or more angles surfaces or wedges 332 designed to cooperate with angled surfaces or ramps 334 on second translation member 320. Longitudinal movement of first translation member 318 causes the distal end of second translation member 320 to move upwards away from lower endplate 314 (while pivoting about the hinge at the proximal end of implant 10). First translation member 318, in turn, causes the distal end 322 of upper endplate 312 to move towards or away from distal end 324 of lower endplate 314.

Similar to previous embodiments, second translation member 318 includes a central bore 350 for receiving an instrument actuator shaft (not shown) that causes longitudinal movement of translation member 318. Also, similar to previous embodiments, implant 10 may include a clicker system for providing discrete steps or increments of angle adjustment. In an exemplary embodiment, the clicker system comprises a series of projections or teeth 352 on support member 316 that cooperate with a series of projections 354 on translation member 318. As translation member 318 moves longitudinally, the projections 354 are configured to move from the space between two teeth 352 to the space between adjoining teeth. These spaces provide the discrete steps or increments. In addition, teeth 352 hold translation member 18 in position relative to endplate 12 to maintain a particular angle between the upper and lower endplates. The projections also inhibit reverse movement (i.e., distal movement) of translation member 18 relative to the endplates.

Similar to previous embodiments, implant 300 may include a number of features that couple the components together and/or stabilize the implant during angle adjustment. In an exemplary embodiment, translation member 320 includes one or more projections, such as conical pins 360, extending through openings 362 in upper endplate 312. Lower endplate 314 may also include openings or projections for coupling to one or more of the components of implant 300.

Figure 23:
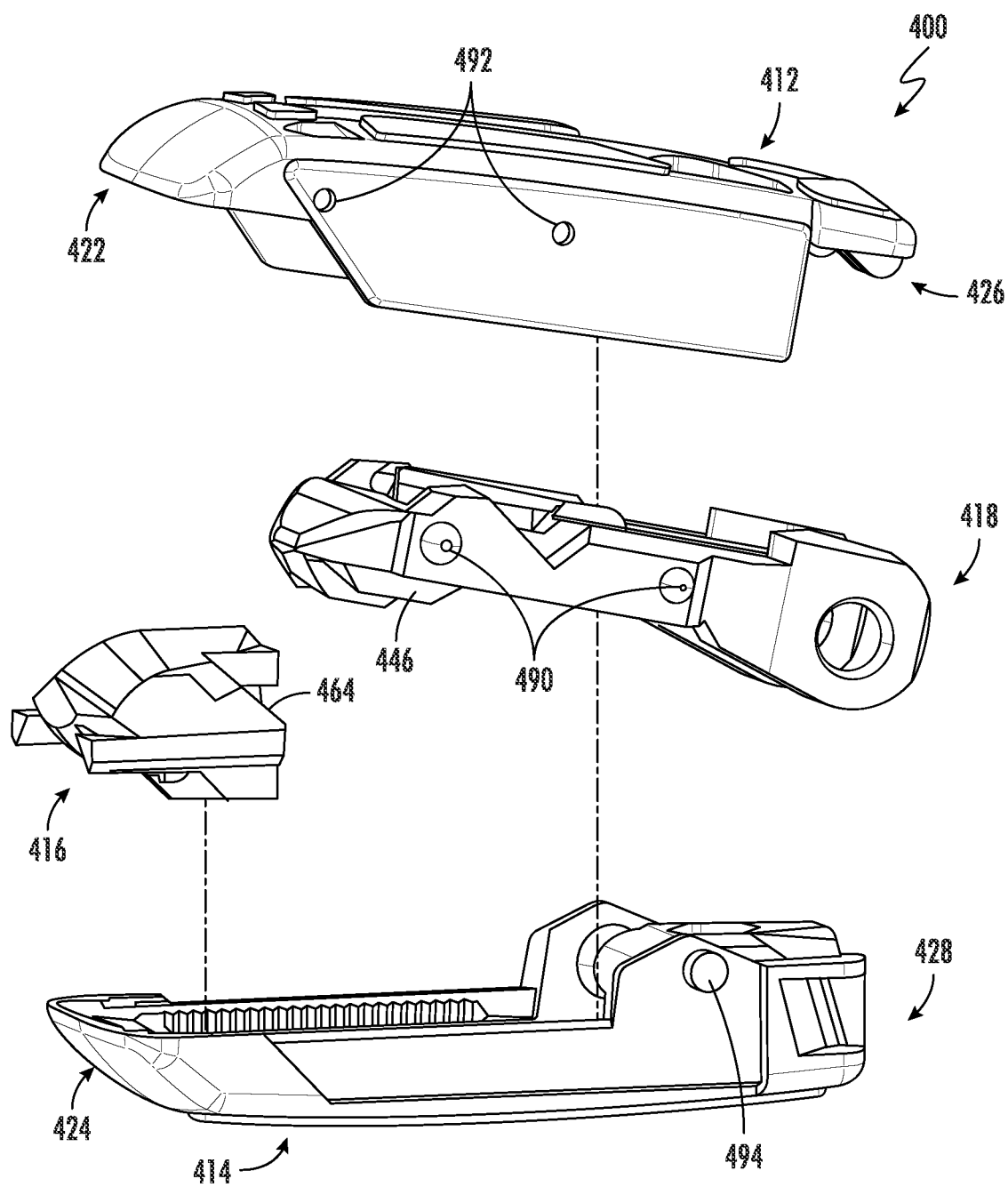
FIG. 23 is an exploded view of the device of FIG. 21.

Referring now to FIGS. 21-27, another embodiment of a spinal implant 400 will now be described. Implant 400 is similar in many features to implant 300. As shown in FIG. 23, implant 400 includes upper and lower endplates 412, 414, a translation member 416 and a pivotable support member 418. As in the previous implant 300, the angle between upper and lower endplates 412, 414 may be adjusted. However, the height or distance between the endplates is not adjustable. More specifically, the distance between distal ends 422, 424 of endplates 412, 414 may be adjusted whereas the distance between proximal ends 426, 428 generally remains fixed.

Support member 418 may be coupled to, or integral with, upper endplate 412. Support member 418 is pivotally coupled to lower endplate 314 with a hinge located near the proximal ends of endplates 312, 314. This hinge allows support member 418 and upper endplate 412 to pivot relative to lower endplate 414 around an axis substantially perpendicular to the longitudinal axis of implant 400. In an exemplary embodiment, support member 418 includes first and second proximal arms 430, 432 laterally spaced from each other and each having an opening 434 therethrough (see FIG. 26). Lower endplate 414 includes a central main body 440 and side walls 442, 444 (see FIG. 24). Main body 440 is spaced from side walls 442, 444 to form first and second channels or gaps 446, 448 therebetween for receiving first and second arms 430, 432 of support member 418. Lower endplate 414 further includes first and second projections 450, 452 extending inwardly from walls 442, 444 towards main body 440 within gaps 446, 448. Projections 450, 452 also extend into openings 434 in arms 430 432 of support member 418 and are designed to cooperate with these openings in support member 418 to form the hinge.

Figure 24:
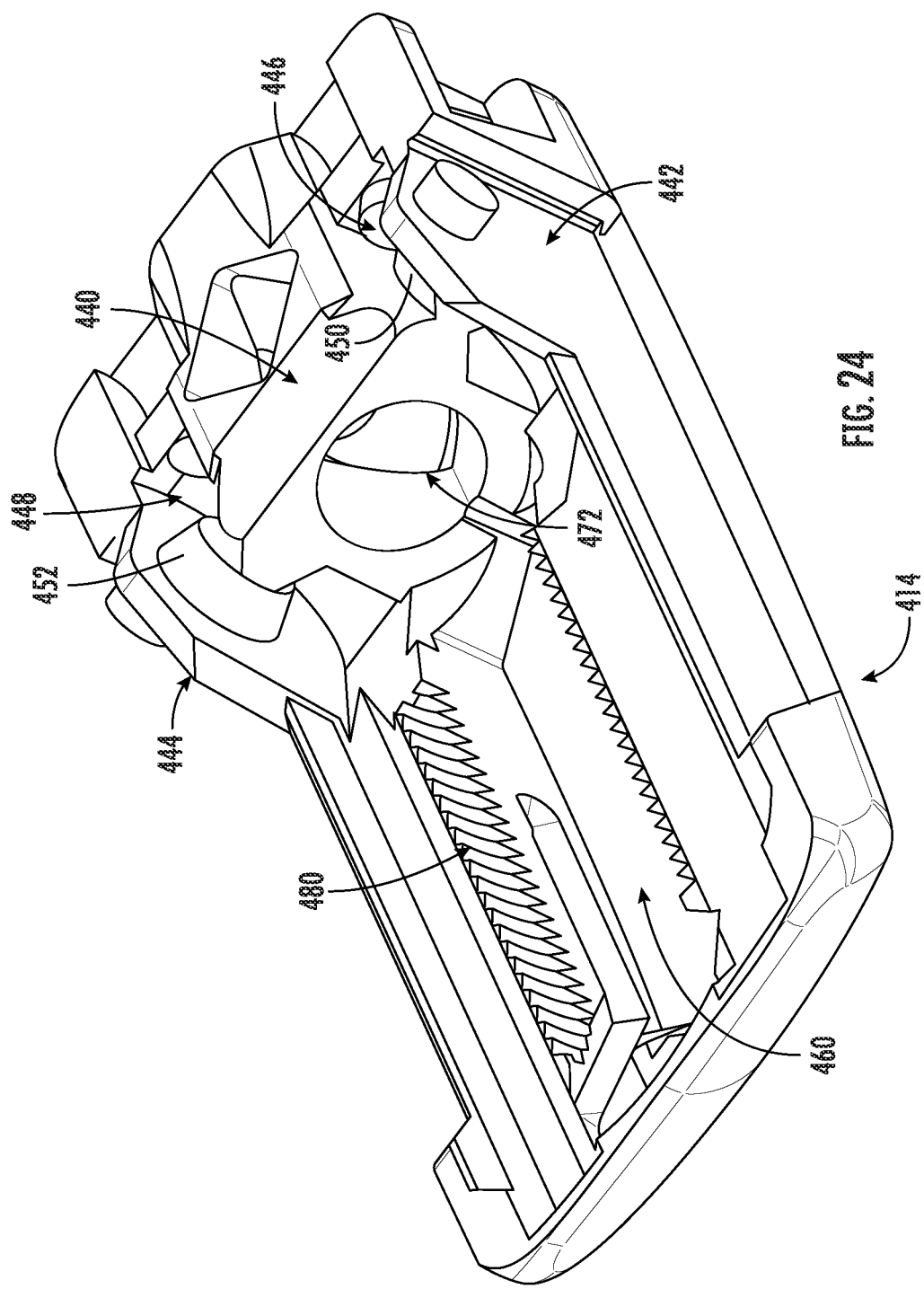
FIG. 24 illustrates a lower endplate of the device of FIG. 21
Figure 25:
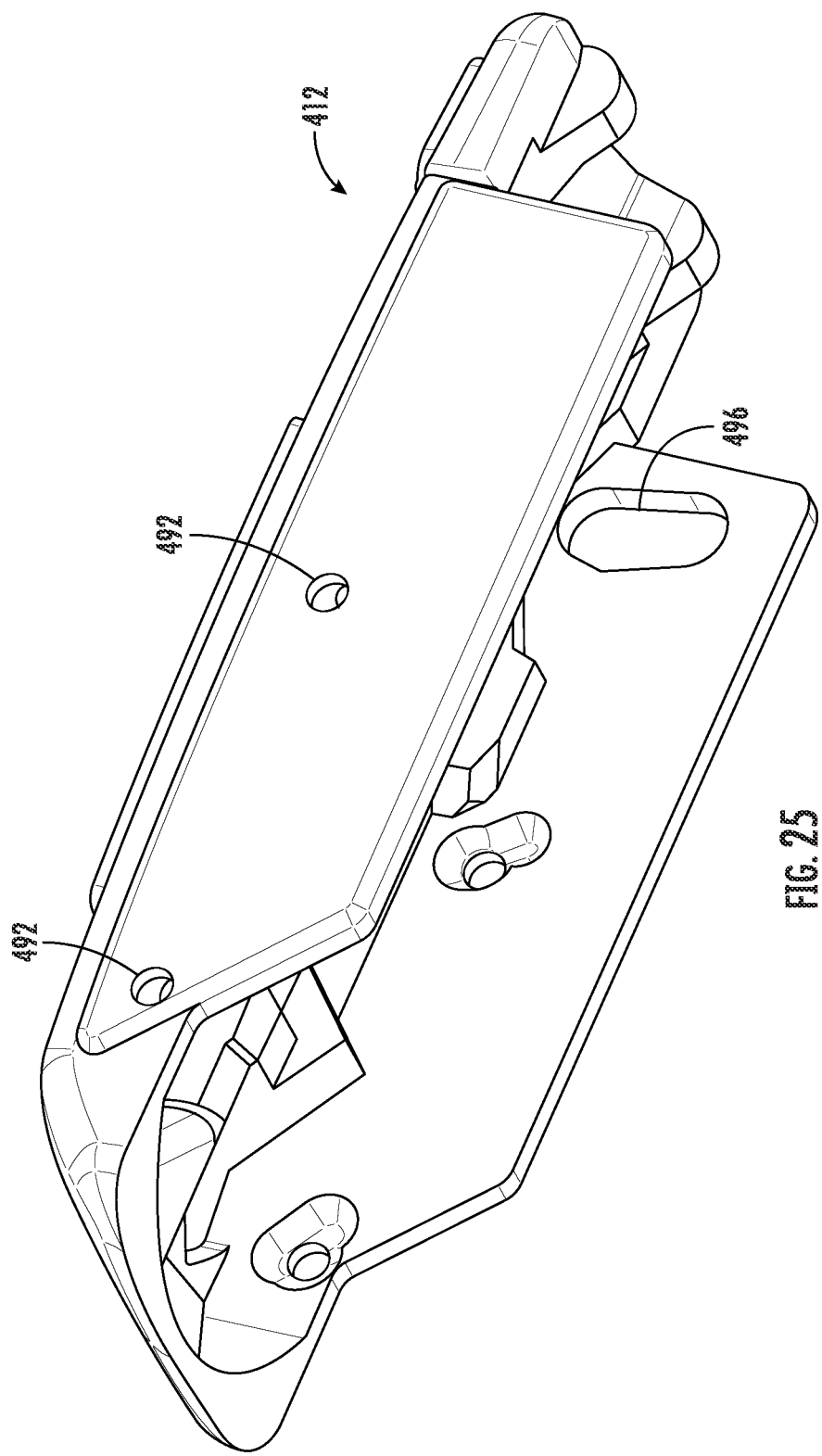
FIG. 25 illustrates an upper endplate of the device of FIG. 21.
Figure 26:
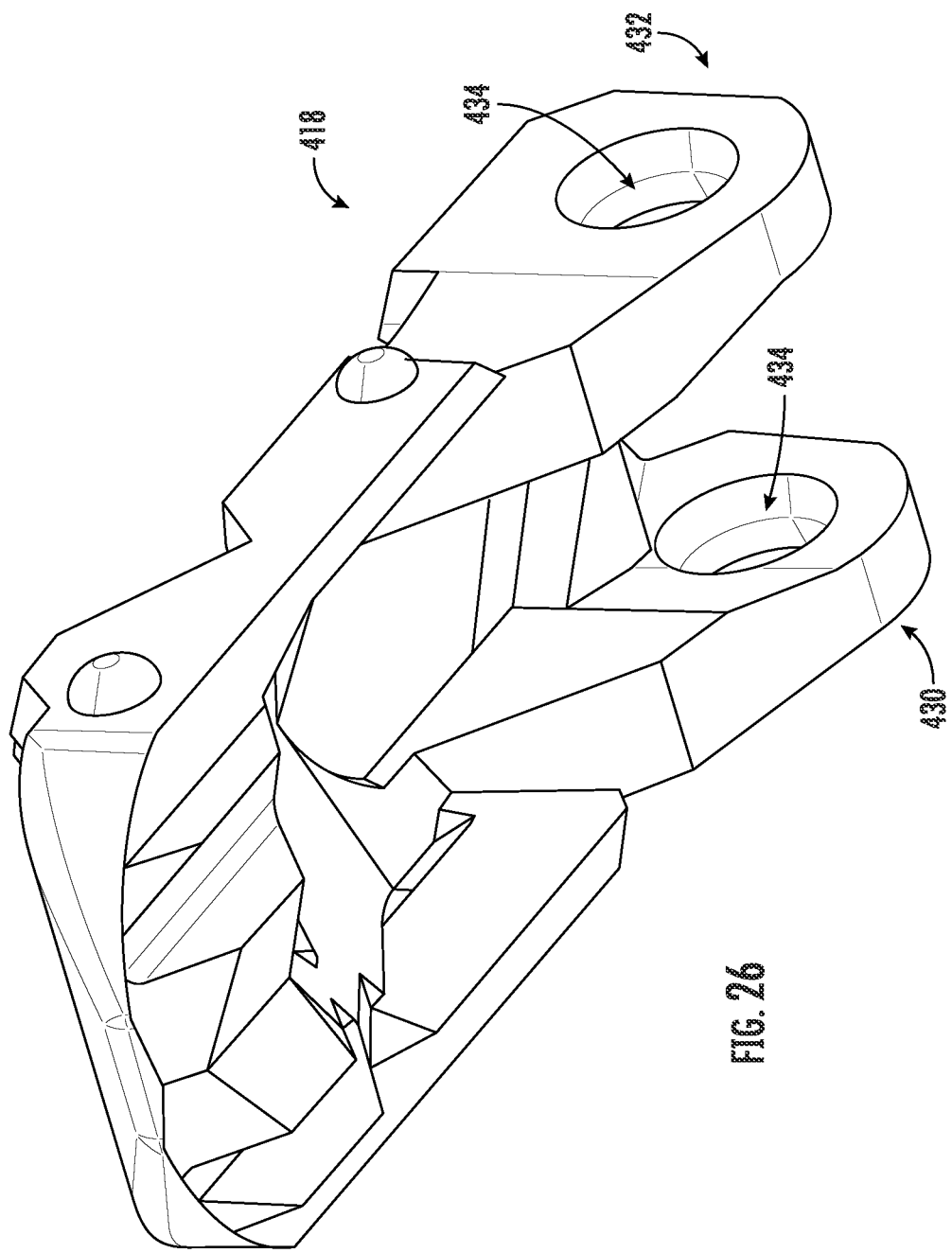
FIG. 26 illustrates an inner support member of the device of FIG. 21.
Figure 27:
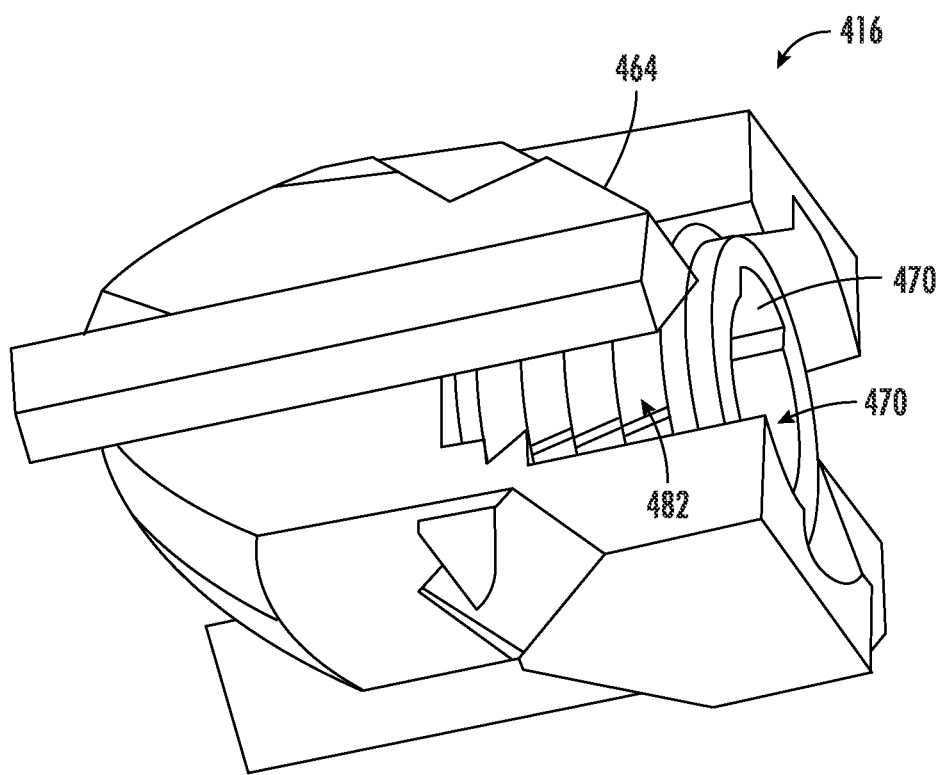
FIG. 27 illustrates an angle translation member of the device of FIG. 21.
Figure 28:
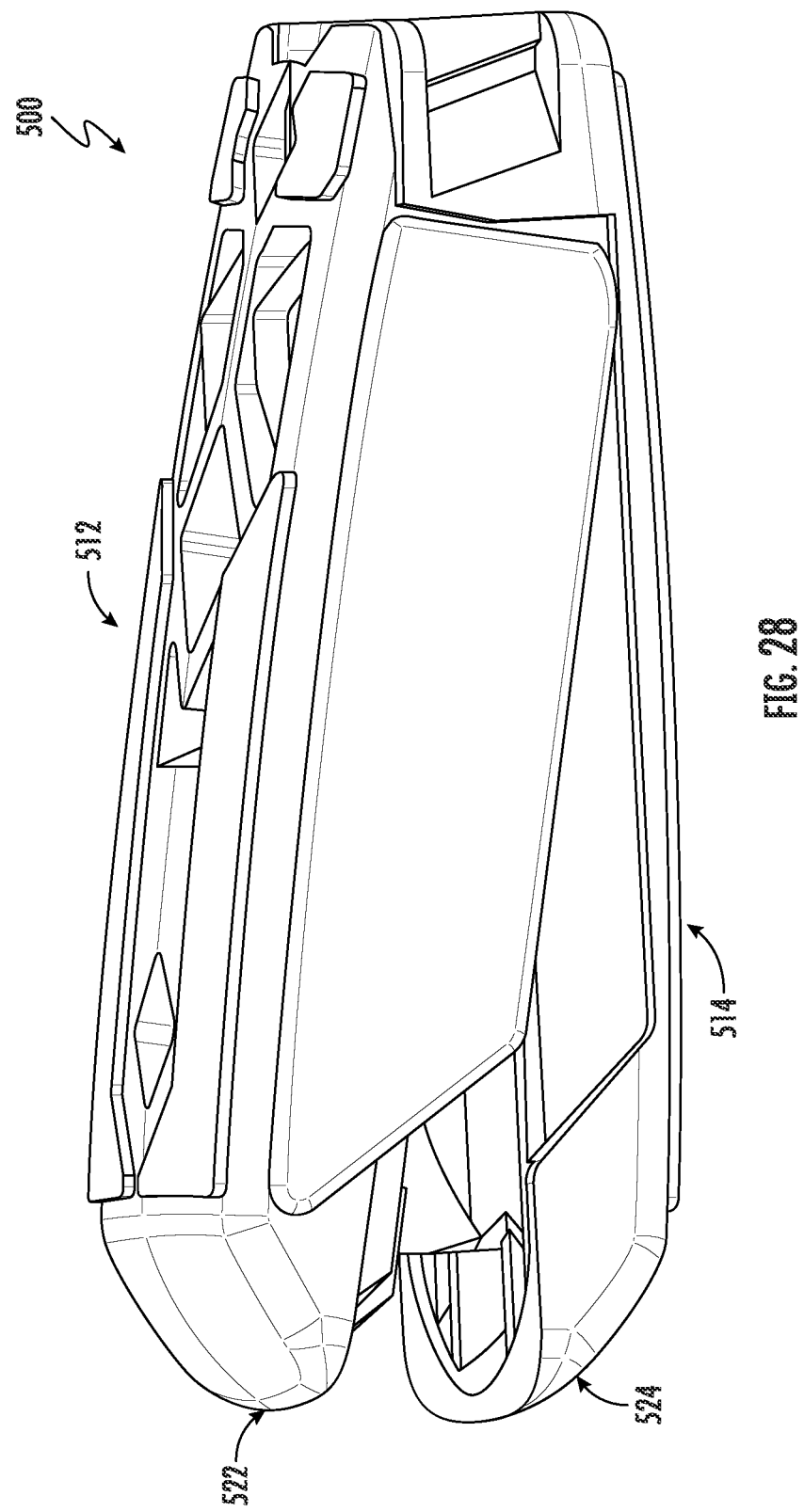
FIG. 28 is a perspective view of another embodiment of a spinal device.
Figure 29:
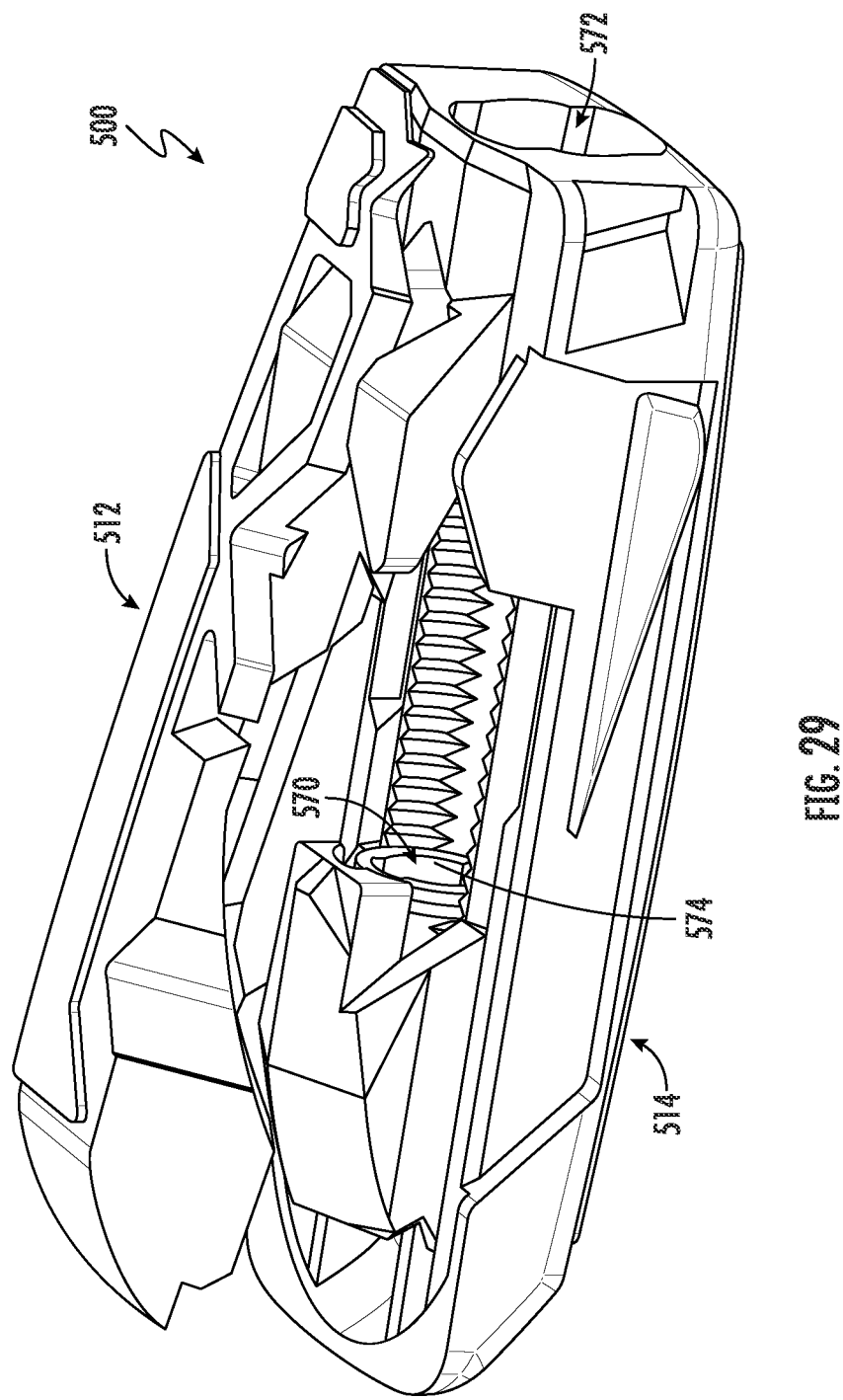
FIG. 29 is a partially cut-a-way view of the device of FIG. 28.

As shown in FIG. 24, lower endplate 414 includes a central channel 460 for receiving translation member 416. Translation member 416 is movable in the longitudinal direction within channel 460 relative to endplates 312, 314 and support member 418 Similar to previous embodiments, translation member 416 includes one or more angles surfaces or wedges 464 designed to cooperate with angled surfaces or ramps 446 on support member 418. Longitudinal movement of translation member 416 causes the distal end of support member 418 to move upwards away from lower endplate 414 (while pivoting about the hinge at the proximal end of implant 400). Support member 418, in turn, causes the distal end 422 of upper endplate 412 to move towards or away from distal end 424 of lower endplate 414.

Similar to previous embodiments, translation member 416 includes a central bore 470 for receiving an instrument actuator shaft (not shown) that causes longitudinal movement of translation member 416. Lower endplate 414 may also include a central bore 472 at its proximal end for receiving the actuator shaft, which passes through bore 472 and central channel 460 of lower endplate 414 to cooperate with a mating feature 474 in bore 470. The mating feature may be similar to those described above.

Also, similar to previous embodiments, implant 400 may include a clicker system for providing discrete steps or increments of angle adjustment. In an exemplary embodiment, the clicker system comprises a series of projections or teeth 480 within channel 460 of lower endplate 414 that cooperate with a series of projections 482 on translation member 416. As translation member 416 moves longitudinally, the projections 482 are configured to move from the space between two teeth 480 to the space between adjoining teeth. These spaces provide the discrete steps or increments. In addition, teeth 480 hold translation member 416 in position relative to endplate 412 to maintain a particular angle between the upper and lower endplates. The projections also inhibit reverse movement (i.e., distal movement) of translation member 416 relative to the endplates.

Similar to previous embodiments, implant 400 may include a number of features that couple the components together and/or stabilize the implant during angle adjustment. In an exemplary embodiment, support member 418 includes one or more projections, such as conical pins 490, extending through openings 492 in upper endplate 412. Lower endplate 414 may also include projections 494 for coupling to one or more openings or slots 496 in upper endplate 412.

Figure 30:
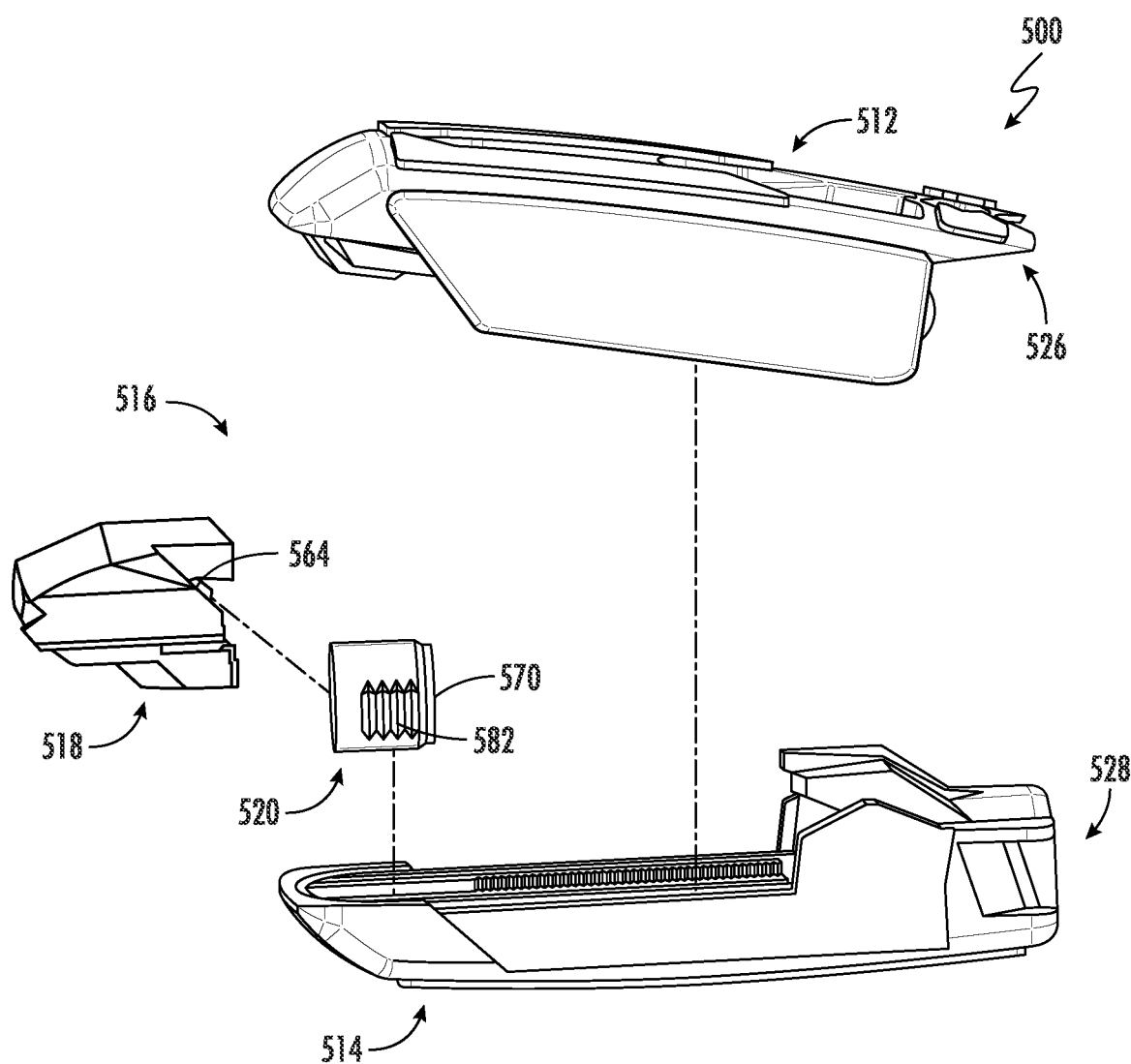
FIG. 30 is an exploded view of the device of FIG. 28.
Figure 31:
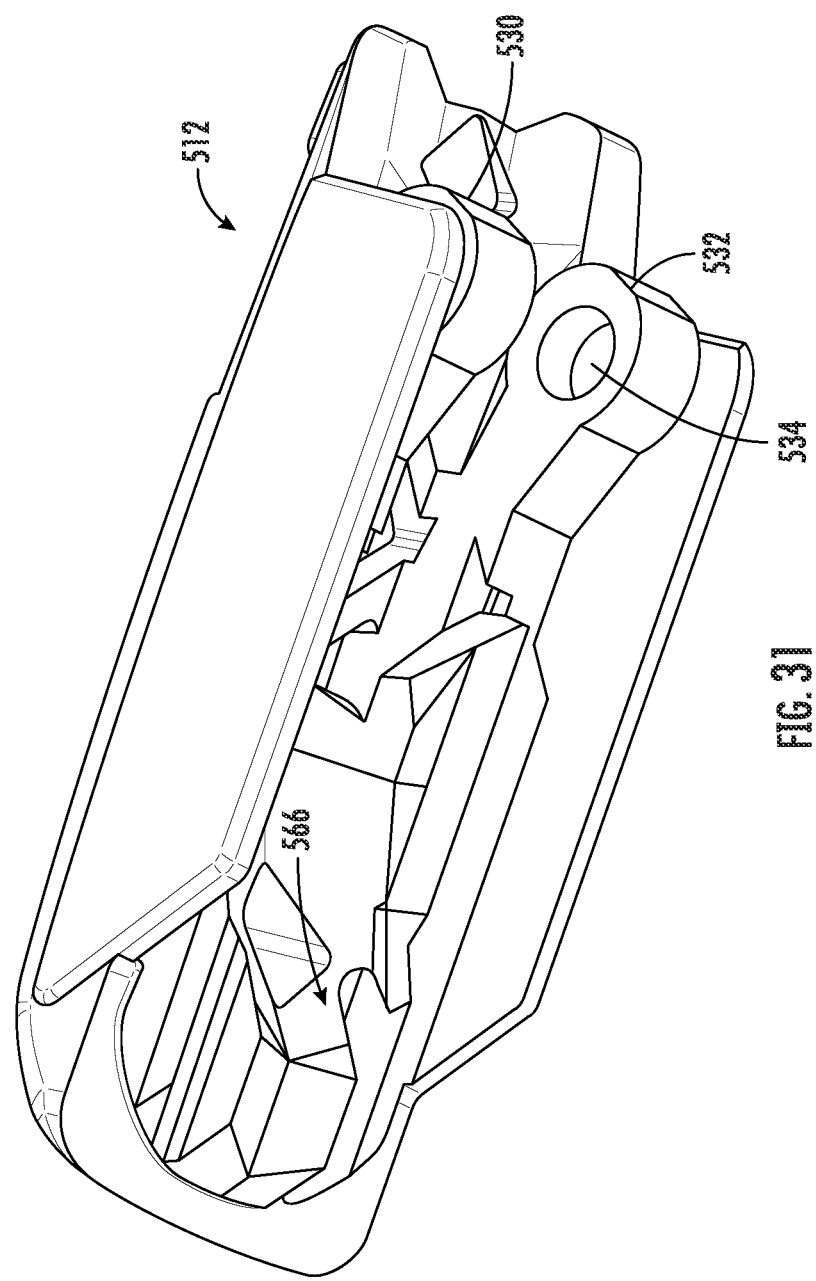
FIG. 31 illustrates an upper endplate of the device of FIG. 28.

Referring now to FIGS. 28-32, another embodiment of a spinal implant 500 will now be described. Implant 500 is similar in many features to implant 400 and implant 300. As shown in FIG. 30, implant 500 includes upper and lower endplates 512, 514 and a translation member 516. In this embodiment, there is no additional support member. The features of support member 418 of the previous embodiment are incorporated into upper endplate 512. As in the previous implant 400, the angle between upper and lower endplates 512, 514 may be adjusted. However, the height or distance between the endplates is not adjustable. More specifically, the distance between distal ends 522, 524 of endplates 512, 514 may be adjusted whereas the distance between proximal ends 526, 528 generally remains fixed.

Upper endplate 512 is pivotally coupled to lower endplate 514 with a hinge located near the proximal ends of endplates 512, 514. This hinge allows upper endplate 512 to pivot relative to lower endplate 514 around an axis substantially perpendicular to the longitudinal axis of implant 500. In an exemplary embodiment, upper endplate 514 includes first and second proximal arms 530, 532 laterally spaced from each other and each having an opening 534 therethrough (see FIG. 31). Lower endplate 514 includes a central main body 540 and side walls 542, 544 (see FIG. 32). Main body 540 is spaced from side walls 542, 544 to form first and second channels or gaps 546, 548 therebetween for receiving first and second arms 530, 532 of support member 518. Lower endplate 514 further includes first and second projections 550, 552 extending outwardly from main body 540 towards side walls 542, 544 within gaps 546, 548. Projections 550, 552 also extend into openings 534 in arms 530 532 of upper endplate 512 and are designed to cooperate with these openings to form the hinge.

Figure 32:
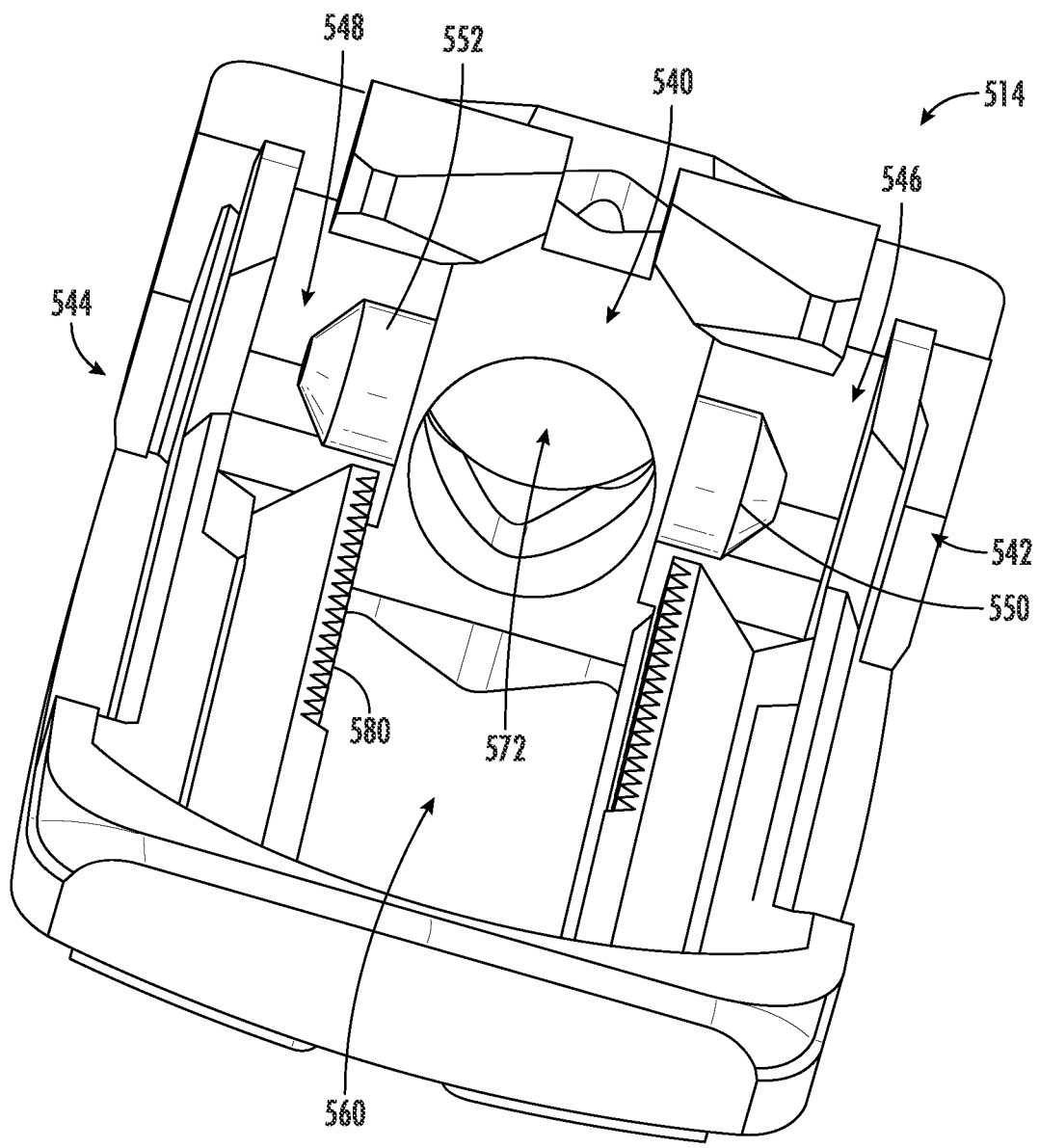
FIG. 32 illustrates a lower endplate of the device of FIG. 28.

As shown in FIG. 32, lower endplate 514 includes a central channel 560 for receiving member 516. Translation member 616 is movable in the longitudinal direction within channel 660 relative to endplates 512, 514. Similar to previous embodiments, translation member 516 includes one or more angles surfaces or wedges 564 designed to cooperate with angled surfaces or ramps 566 on upper endplate 512 Longitudinal movement of translation member 516 causes the distal end of upper endplate 512 move towards or away from lower endplate 514 (while pivoting about the hinge at the proximal end of implant 500).

As shown in FIG. 30, translation member 516 includes a main body 518 coupled to, or integral with, a cylindrical ratchet member 520. Ratchet member 520 comprises a central bore 570 for receiving an instrument actuator shaft (not shown) that causes longitudinal movement of translation member 516. Lower endplate 514 may also include a central bore 572 at its proximal end for receiving the actuator shaft, which passes through bore 572 and central channel 560 of lower endplate 514 to cooperate with a mating feature 574 in bore 570. The mating feature may be similar to those described above.

Also, similar to previous embodiments, implant 500 may include a clicker system for providing discrete steps or increments of angle adjustment. In an exemplary embodiment, the clicker system comprises a series of projections or teeth 580 within channel 560 of lower endplate 514 that cooperate with a series of projections 582 on translation member 516. As translation member 516 moves longitudinally, the projections 582 are configured to move from the space between two teeth 580 to the space between adjoining teeth. These spaces provide the discrete steps or increments. In addition, teeth 580 hold translation member 516 in position relative to endplate 512 to maintain a particular angle between the upper and lower endplates. The projections also inhibit reverse movement (i.e., distal movement) of translation member 516 relative to the endplates.

Similar to previous embodiments, implant 500 may include a number of features that couple the components together and/or stabilize the implant during angle adjustment.

Figure 33:
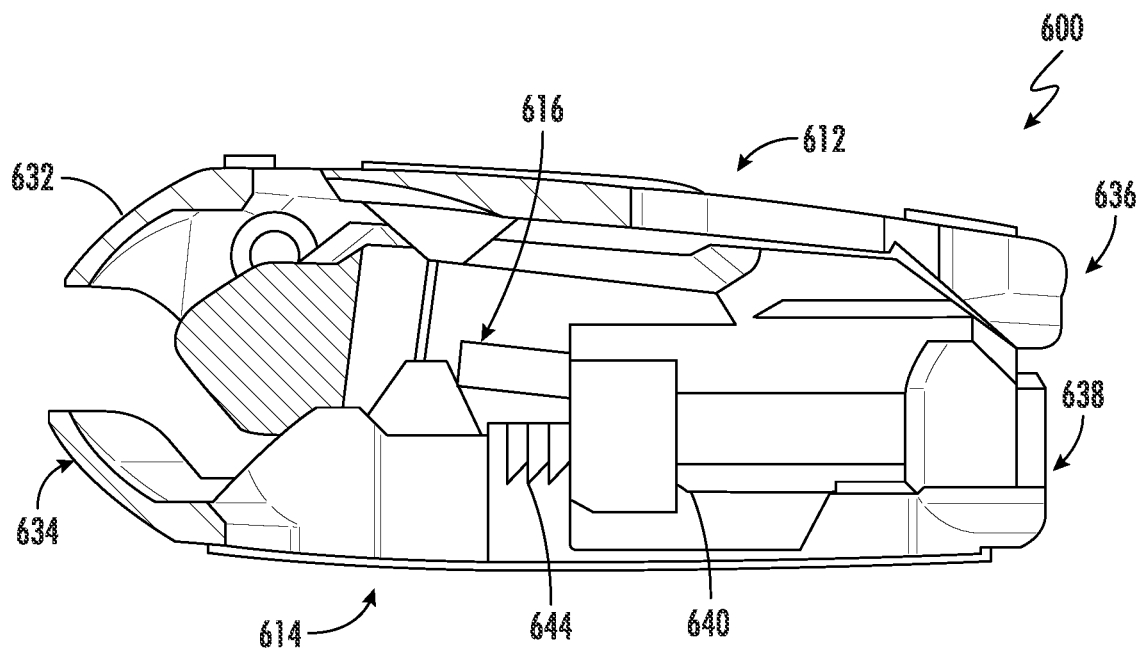
FIG. 33 is a partially cut-a-way view of another embodiment of a spinal device.
Figure 34:
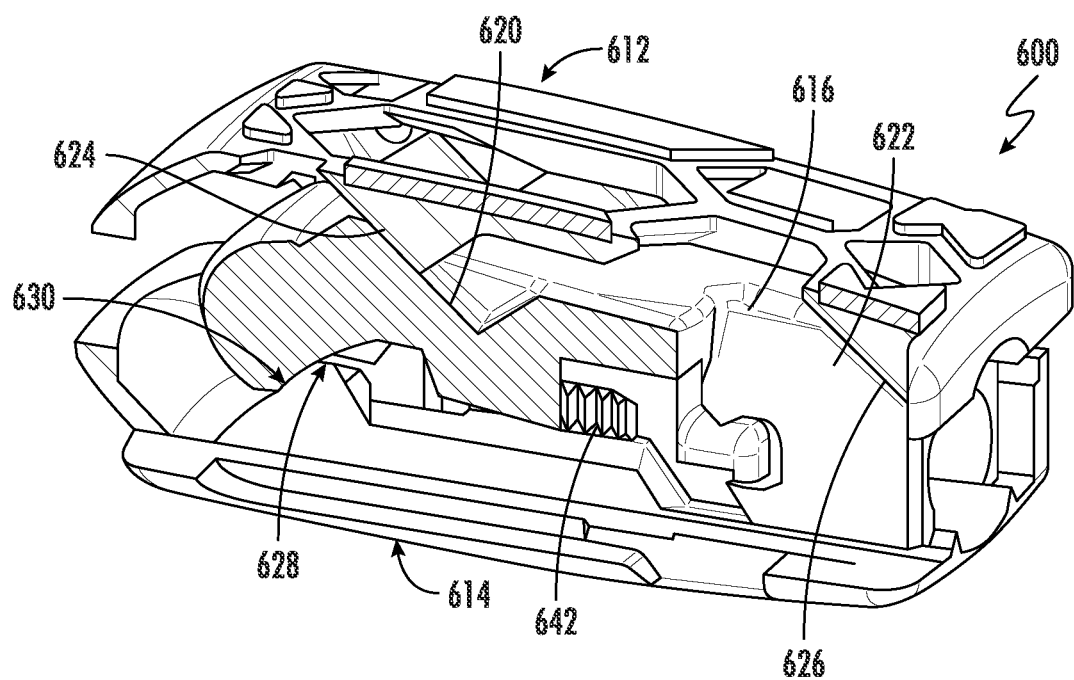
FIG. 34 is another view of the spinal device of FIG. 33.

Referring now to FIGS. 33 and 34, another embodiment of a spinal implant 600 comprises upper and lower endplates 612, 614 and a translation member 616. Implant 600 has many similar features and elements as the previous embodiments. In this embodiment, however, translation member 616 is configured to adjust both the angle and height of endplates 612, 614 as it is moved longitudinally relative to endplates 612, 614.

As shown in FIG. 34, translation member 616 includes first and second distal angled surfaces or wedges 620 and first and second proximal angled surfaces or wedges 622. The distal and proximal wedges 620, 622 extend downward from upper endplate 612 in the proximal direction and are spaced from each other laterally relative to the longitudinal axis of implant 600 (note that only one of the distal and proximal wedges 620, 622 is shown). Upper endplate 614 also includes first and second distal angled surfaces or ramps 624 and first and second distal angled surfaces or ramps 626 (again only one of each of these ramps is shown). As in previous embodiments, longitudinal movement of translation member 616 causes the wedges to contact the ramps and move upper endplate 612 towards and away from lower endplate 614.

Transition member 616 further includes two lower distal wedges 628 extending upward towards upper endplate 612 in the proximal direction and laterally spaced from each other. Similarly, lower endplate 614 includes two distal angled surfaces or ramps 630 extending upwards towards upper endplate 614 in the proximal direction (only one of each ramp and wedge is shown). Longitudinal movement of transition member 616 causes wedges 628 to contact ramps 630 such that distal ends 632, 634 of endplates 612, 614 move towards and away from each other. Since proximal ends 636, 638 of endplates 612, 614 do not move relative to each other in conjunction with distal ends 632, 634, this causes the overall angle of endplates 612, 614 to change. Note that while proximal ends 636, 638 do move upwards with the overall increase in height, this movement is coordinates with movement of distal ends 632, 634. However, distal ends 632, 634 move further away from each other than proximal ends 636, 638 resulting in an adjustment of angle between endplates 612, 614.

Similar to previous embodiments, translation member 616 includes an internal bore 640 for receiving, and mating with, a shaft actuator (not shown) of an instrument shaft. The shaft actuator causes longitudinal movement of translation member 616. Similar to previous embodiments, implant 600 may include a number of features that couple the components together and/or stabilize the implant during angle adjustment.

Also similar to previous embodiments, translation member 616 includes a ratchet shaft 642 that cooperates with projections or teeth 644 on lower endplate 614 to provide discrete steps or increments of height and/or angle adjustment.

The entire implant is fabricated through additive manufacturing techniques, such as 3D printing. The implant is formed layer by layer in the longitudinal direction from the proximal end to the distal end. Upon completion of manufacturing, the upper and lower endplates are substantially separated from each other except for their distal end portions. These portions are separated through wire EDM by cutting a substantially vertical line through these portions to form two separate components. In the Spring component, the endplates remain coupled together solely by the leaf spring. The endplates retain positional stability relative to each other during use through the conical knobs in the proximal translation member that slide through angled slots in the endplates, the conical knobs in the lower endplate that slide through the vertical slots in the upper endplate (Slot embodiment) and the leaf spring (Spring Embodiment).

In an exemplary embodiment, the implants are produced by Selective Laser Melting (SLM). For example, a substrate plate is fastened to an indexing table inside a chamber with a controlled atmosphere of inert gas (e.g., argon or nitrogen). Metal powder is applied flat to the substrate plate as a layer. The metal powder is preferably a titanium alloy, e.g. Ti-6Al-4V to enable biocompatibility. Each 2D slice of the cage is fused by selectively melting the metal powder via a laser. The laser has enough energy to fully melt or rather weld the metal particles to form solid metal. The substrate plate is lowered by the layer thickness (z-direction). New metal powder is applied and the process is repeated layer by layer until the part is complete. The completed part is removed from the substrate plate by cutting or breaking off.

Preferably, all components of the cage are printed nested within each other. Compared to separately 3D printing all components next to each other, a higher utilization rate can be achieved. This means that during 3D printing, a higher proportion which is melted and a lower proportion which stays as metal powder can be achieved. Thus, production time and costs can be reduced significantly.

After 3D printing, areas connecting single components of the cage are cut by electrical discharge machining (EDM) to enable their separate movement. Further, EDM can be used to realize smooth surfaces, e.g., to enable low-friction sliding of two components against each other. With EDM, the cage can also be removed from the substrate plate.

To lower production costs, several cages can be printed onto one substrate plate. In this case, before removing the cages, EDM can be used to simultaneously cut all cages placed on the substrate plate.

The implant may comprise one or more exhaust openings in the upper and lower endplates to allow for extraction of the metal powder remaining in the cage after 3D printing. Preferably, the exhaust opening is positioned on a lateral surface of the moving plate. It is also possible to position the exhaust opening on a horizontal surface of the cage, preferably on the base plate or on the moving plate. Preferably, the cage comprises multiple exhaust openings. Thus, more areas inside the cage are reachable and the metal powder can be extracted more efficiently. It is also possible to configure an external sliding mean, preferably a conical groove, in such a way that it can be additionally used as an exhaust opening. Therefore, the conical groove is deepened until a passage to the outside has been made.

Other embodiments will be apparent to those skilled in the art from consideration of the specification and practice of the embodiment disclosed herein. It is intended that the specification and examples be considered as exemplary only, with a true scope and spirit of the embodiment being indicated by the following claims.

What is claimed is:

1. An adjustable spinal fusion device, comprising:
an upper endplate having proximal and distal ends, and an outer surface for placement against a first vertebral body;
a lower endplate having proximal and distal ends, and an outer surface for placement against a second vertebral body;
a translation member configured to move proximally relative to the upper and lower endplates to adjust an angle between the upper and lower endplates by moving the distal end of the upper endplate away from the distal end of the lower endplate and maintaining a fixed distance between the proximal end of the upper endplate and the proximal end of the lower endplate, wherein the translation member comprises an angled surface extending downward from the upper endplate towards the lower endplate in the proximal direction, the device further comprising a ramp for cooperating with the angled surface of the translation member such that proximal movement of the translation member moves the distal ends of the endplates further apart; and
an internal support member coupled to, or integral with, the upper endplate and a hinge pivotally coupling the internal support member to the lower endplate, wherein the ramp is on the internal support member, further wherein the internal support member comprises at least one projection extending laterally away from the internal support member, and the upper endplate comprises at least one opening for receiving the at least one projection.

2. The adjustable spinal fusion device of claim 1, wherein the translation member comprises a bore with a mating feature for receiving a surgical instrument to effect movement in the longitudinal direction.

3. The adjustable spinal fusion device of claim 1, wherein the proximal ends of the first and second endplates are pivotally coupled to each other.

4. The adjustable spinal fusion device of claim 1, wherein said proximal movement of the translation member causes the angled surface to engage the ramp and move the distal end of the upper endplate away from the distal end of the lower endplate, and wherein the proximal ends of the endplates remain substantially fixed relative to each other as the distal ends are moved apart.

5. The adjustable spinal fusion device of claim 1, wherein the translation member comprises a plurality of projections and one of the upper or lower endplates comprise a plurality of teeth that cooperate with the projections, wherein the projections move relative to the teeth as the translation member is moved longitudinally.

6. A spinal fusion system, comprising:
an adjustable spinal fusion device comprising:
an upper endplate having an outer surface for placement against a first vertebral body;
a lower endplate having an outer surface for placement against a second vertebral body;
a translation member configured to move proximally relative to the upper and lower endplates to adjust an angle between the upper and lower endplates by moving a distal end of the upper endplate relative to a distal end of the lower endplate and maintaining a fixed distance between a proximal end of the upper endplate and a proximal end of the lower endplate, wherein the translation member comprises an angled surface extending downward from the upper endplate towards the lower endplate in the proximal direction, the device further comprising a ramp for cooperating with the angled surface of the translation member such that proximal movement of the translation member moves the distal ends of the endplates further apart;
an internal support member coupled to, or integral with, the upper endplate and a hinge pivotally coupling the internal support member to the lower endplate, wherein the ramp is on the internal support member, and wherein the internal support member comprises at least one projection extending laterally away from the internal support member, and the upper endplate comprises at least one opening for receiving the at least one projection; and
an instrument having a proximal handle, an elongate shaft, and an actuator within the elongate shaft coupled to the proximal handle, to cooperate with the translation member for moving the first translation member longitudinally relative to the upper and lower endplates.

7. The system of claim 6, wherein the translation member comprises a bore with a first mating feature and the distal end of the actuator comprises a second mating feature, the first and second mating features cooperating with each other such that longitudinal movement of the actuator causes distal ends of the endplates to move relative to each other to adjust a distance therebetween.

8. The system of claim 6, wherein the translation member comprises a plurality of projections and one of the upper or lower endplates comprise a plurality of teeth that cooperate with the projections, wherein the projections move relative to the teeth as the translation member is moved longitudinally.

* * * * *